US008247615B2

(12) United States Patent
Reilly et al.

(10) Patent No.: US 8,247,615 B2
(45) Date of Patent: Aug. 21, 2012

(54) **PROCESS OF CONVERTING ESTERIFIED XANTHOPHYLLS FROM *CAPSICUM* TO NON-ESTERIFIED XANTHOPHYLLS IN HIGH YIELDS AND PURITIES**

(75) Inventors: Mark Reilly, Kalamazoo, MI (US); Josh James Tuinstra, Plainwell, MI (US); Lucas Chadwick, Ann Arbor, MI (US); Mark Porter, Kalamazoo, MI (US); James Barren, Kalamazoo, MI (US); Gregory S. Reynhout, Kalamazoo, MI (US)

(73) Assignee: Kalamazoo Holdings, Inc., Kalamazoo, MI (US)

( * ) Notice: Subject to any disclaimer, the term of this patent is extended or adjusted under 35 U.S.C. 154(b) by 215 days.

(21) Appl. No.: 12/800,416

(22) Filed: May 14, 2010

(65) Prior Publication Data

US 2011/0282083 A1    Nov. 17, 2011

(51) Int. Cl.
*C07C 35/21* (2006.01)
*C07C 27/02* (2006.01)
*C07D 303/14* (2006.01)
(52) U.S. Cl. ................. 568/367; 568/816; 549/547
(58) Field of Classification Search ............... 568/367, 568/816; 549/547
See application file for complete search history.

(56) References Cited

U.S. PATENT DOCUMENTS

| | | | |
|---|---|---|---|
| 2,849,507 | A | 8/1958 | Isler |
| 3,206,316 | A | 9/1965 | Klaui |
| 3,441,623 | A | 4/1969 | Surmatis |
| 3,523,138 | A | 8/1970 | Grant |
| 3,989,757 | A | 11/1976 | Surmatis |
| 4,883,887 | A | 11/1989 | Bernhard |
| 5,382,714 | A | 1/1995 | Khachik |
| 5,523,494 | A | 6/1996 | Torres-Cardona |
| 5,602,286 | A | 2/1997 | Muralidhara |
| 5,648,564 | A * | 7/1997 | Ausich et al. ............ 568/834 |
| 5,847,238 | A | 12/1998 | Muralidhara |
| 5,876,782 | A | 3/1999 | Sas |
| 5,973,211 | A | 10/1999 | Rodriguez |
| 5,998,678 | A | 12/1999 | Sanroma |
| 6,110,478 | A | 8/2000 | Harang |
| 6,191,293 | B1 | 2/2001 | Levy |
| 6,221,417 | B1 | 4/2001 | Sas |
| 6,262,284 | B1 | 7/2001 | Khachik |
| 6,329,432 | B2 | 12/2001 | Howard |
| 6,329,557 | B1 | 12/2001 | Rodriguez |
| 6,376,722 | B1 | 4/2002 | Sanz |
| 6,380,442 | B1 | 4/2002 | Madhavi |
| 6,504,067 | B1 | 1/2003 | Montoya |
| RE38,009 | E | 2/2003 | Garnett |
| 6,743,953 | B2 | 6/2004 | Kumar |
| 6,747,177 | B2 | 6/2004 | Ernst |
| 6,784,351 | B2 | 8/2004 | Hauptmann |
| 6,797,303 | B2 | 9/2004 | Zelkha |
| 7,109,361 | B2 | 9/2006 | Hoffman |
| 7,150,890 | B2 | 12/2006 | Rosales |
| 7,173,145 | B2 | 2/2007 | Khachik |
| 7,179,930 | B2 | 2/2007 | Bhaskaran |
| 7,691,406 | B2 | 4/2010 | Garnett |
| 2003/0108598 | A1 | 6/2003 | Garnett |
| 2005/0139145 | A1 | 6/2005 | Quesnel |
| 2006/0185034 | A1 * | 8/2006 | Todd et al. ............ 800/282 |
| 2007/0032683 | A1 | 2/2007 | Xu |
| 2007/0161826 | A1 | 7/2007 | Pena |

FOREIGN PATENT DOCUMENTS

| | | |
|---|---|---|
| CN | 1436774 | 8/2003 |
| ES | 2265787 | 2/2007 |
| JP | 57133160 | 8/1982 |
| JP | 57180663 | 11/1982 |
| JP | 58173164 | 10/1983 |
| WO | WO97/23436 | 7/1997 |
| WO | WO0016792 | 3/2000 |
| WO | WO01/94279 | 12/2001 |
| WO | WO02/060865 A1 * | 8/2002 |
| WO | WO02060865 | 8/2002 |
| WO | WO2004/018417 | 3/2004 |
| WO | WO2006114794 | 11/2006 |

OTHER PUBLICATIONS

Abel, Robert Jr. The Eye Care Revolution Kensington Publishing Corp. New York, New York, Chapter 8. p. 158, 1999.
Ahmed, et al. Survey of Opthamology 50:183-193, 2005.
Alves-Rodriguez, et al. Toxicology Letters 150:57-83, 2004.
Beatty, et al. Archives of Biochemistry and Biophysics 430:70-76, 2004.
Brown, et al. American Society for Clinical Nutrition 70:517-24, 1999.
Chew, et al. Anticancer Research 16:3689-3694, 1996.
Chopra , et al. Abstracts of Communications 18A, 1993.
Conner, et al. Journal of the American Dietetic Association, 104:1793-1799, 2004.
Craft, et al. J. Agric. Food Chem. 40:431-434, 1992.
Curl Agricultural and Food Chemistry 1:456-460, 1953.
Curl Agricultural and Food Chemistry 10:504-509, 1962.
Curl Agricultural and Food Chemistry 12:522-524, 1964.
Davies, et al. Progress in Retinal Eye Research 23:533-559, 2004.
Englert, et al. Helvetica Chemica Acta 74:959-982, 1991.
Granado, et al. J. Agric. Food Chem. 40:2135-2140, 1992.

(Continued)

*Primary Examiner* — Sikarl Witherspoon
(74) *Attorney, Agent, or Firm* — Hueschen and Sage

(57) ABSTRACT

The present invention is concerned with a process to convert xanthophyll esters derived from *Capsicum* sources to their free (non-esterified) forms. The present invention is concerned with a process for obtaining *Capsicum* derived xanthophylls that meet the finished product needs for purity, yield, ease of use, industrial compatibility and cost that are required to make product suitable for the nutritional supplement, food and beverage industries. The present invention is concerned with a process which yields from 60 to 80%, of xanthophyll materials and nearly quantitative recovery of all input xanthophylls, which xanthophylls are of high purity. The present invention concerns a method to obtain xanthophyll esters present almost exclusively in the trans form when isolated from the natural plant sources. The present invention concerns a process to re-convert cis product back to the more desired trans form.

25 Claims, 2 Drawing Sheets

OTHER PUBLICATIONS

Granado, et al. Journal of Food Composition and Analysis 14:474-489, 2001.
Hart, et al. Food Chemistry 54:101-111, 1995.
Howard, et al. Internat. J. Vit. Nutr. Res. 66:113-118, 1996.
International Preliminary Report on Patentability for PCT/US2010/01587 of Jan. 31, 2012.
International Search Report for PCT/US2010/001587 of Jul. 28, 2010.
Isler, et al. Volumen XXXIX, Fasciculus X, No. 27, pp. 249-259, 1956.
Ito, et al. Journal of Epidemiology vol. 15 (Supplement II) S140-S149, 2005.
Karrer, et al. Chapter V, pp. 38-42, in Carotenoids, Elsevier Publishing Co., Inc. Amsterdam, 1950.
Khachik, et al. Journal of Chromatography 582:153-166, 1992.
Khachik; et al. J. Agric. Food Chem. 34:603-616, 1986.
Khachik, et al. Journal of Cellular Biochemistry (Supplement) 22:236-246, 1995.
Kimura, et al. Food Chemistry 35:187-195, 1990.
Kohlmeier, et al. Am J Clin Nutr (Supplement) 62:1370S-1376S, 1995.
Larsen, et al. J. Agric. Foot Chem, 53:6598-6602, 2005.
Levy, et al. Nutrition and Cancer 24:257-266, 1995.
Lyle, et al. American Journal of Epidemiology 149:801-809, 1999.
Minguez-Mosquera, et al. J. Agric. Food Chem. 41:1616-1620, 1993.
Moeller, et al. Journal of the American College of Nutrition 19:522S-527S, 2000.
Morris, et al. JAMA 272:1439-1441, 1994.
Murakoshi, et al. Cancer Research 52:6583-6587, 1992.
Pattison, et al. American Journal of Clinical Nutrition 82:451-455, 2005.
Ribaya-Mercado, et al. Journal of the American College of Nutrition 23:567S-587S, 2004.
Roberts, et al. Clinics in Dermatology 27:195-201, 2009.
Roche Roche Vitamins Technical Publication HHN-1382/0800, 2000.
Rock, et al. Journal of Clinical Oncology 23:6631-6638, 2005.
Rodriguez-Bernaldo, et al. Journal of Food Composition and Analysis 19:97-111, 2006.
Schieber et al. Trends in Food Science & Technology 16:416-22. 2005.
Scott Food Chemistry 45:357-364, 1992.
Seddon, et al. JAMA 272:1413-1420. 1994.
Stahl Nutrition and the Eye, in Dev. Opthamol. Karger Publishers, Basel Switzerland. vol. 38, pp. 70-88, 2005.
Stringham, et al. Nutrition Reviews 63:59-64, 2005.
Tanaka, et al. Carcinogenesis 15:15-19, 1994.
Tyczkowski, et al. Poultry Science 70:651-654, 1990.
Updike, et al. J. Agric. Food Chem. 1:6184-6190, 2003.
Wingerath, et al. Archives of Biochemistry and Biophysics 324:385-390, 1995.
Written Opinion of the International Searching Authority for PCT/US2010/001587 of May 28, 2010.
Zechmeister, L Cis-Trans Isomeric Carotenoids Vitamins A and Arylpolyenes. Acedemic Press Publishers, New York, New York, pp. 46-47, 1962.

* cited by examiner

PROCESS OF CONVERTING ESTERIFIED XANTHOPHYLLS FROM *CAPSICUM* TO NON-ESTERIFIED XANTHOPHYLLS IN HIGH YIELDS AND PURITIES

FIELD OF THE INVENTION

The present invention relates to a process of converting esterified (non-free form) xanthophylls from *Capsicum* to non-esterified (free form) xanthophylls in high yields and purities. The invention more particularly relates to the isolation processes utilized to optimize both purity and yield to produce material which is suitable for use in the food, nutritional supplement, cosmetics, pharmaceutical and related industries. Additionally, this invention relates to the isolation and purification of carotenes typically found associated with the xanthophylls from natural sources, for similar purposes. Additionally, the present invention relates to processes for obtaining saponified xanthophylls from *Capsicum* extracts, which extracts normally contain relatively high levels of interfering substances, such as waxes, fats and oils, relative to xanthophyll esters.

BACKGROUND OF THE INVENTION

The ripe fruit of *Capsicum* species are a well known, important source of a variety of carotenoids, including two main groups: carotenes and oxygenated carotene derivatives, commonly referred to as xanthophylls. For example, *Capsicum* species can contain capsanthin, capsorubin, cryptoxanthin, zeaxanthin, lutein, and other carotenoids that have substantial nutritional and medicinal value. Carotenoids are yellow, red and orange pigments which are widely distributed in nature. The carotenes refer to those carotenoids which only contain carbon and hydrogen atoms; examples include alpha and beta carotene and lycopene. Xanthophylls refer to carotenoids that contain one or more oxygen atoms, such as zeaxanthin, lutein, capsanthin, capsorubin, astaxanthin, cryptoxanthin, violaxanthin, and antheraxanthin. The hydroxyl-containing carotenoids are often found as esters in the plant material. They usually are found as diesters of fatty acids containing from eight to twenty carbon atoms. Examples of these fatty acids include linoleic, palmitic, oleic, linolenic, myristic, stearic, lauric, and the like.

Epidemiological studies have shown that frequent and regular consumption of carotenoids reduces risks of chronic disorders, such as cardiovascular diseases [Kohlmeier et al., (1995)] or cancer [Murakoshi et al., (1992); Levy et al. (1995); Tanaka et al., 1994); Ito et al. (2005), Connor et al. (2004), and Rock et al. (2005)]. Carotenoids may also function as antioxidants in disease prevention. Carotenoids have been found to be membrane antioxidants perhaps due to their reactivity with singlet oxygen and oxygen free radicals. Singlet oxygen has been shown to be capable of damaging proteins, lipids and DNA in biological systems. The potential cancer chemopreventive activity of carotenoids may be attributable to their antioxidant activity. Free radials generated in the body during metabolism can damage eye tissue. Eye tissue contains polyunsaturated fatty acids, which are susceptible to damage by free radicals and oxidative stress. In eye tissues, antioxidants such as zeaxanthin and lutein help prevent this damage.

Lutein and zeaxanthin are highly concentrated in the macula of the eye, with zeaxanthin being most highly concentrated at the center of the macula. The macula is a small area of the retina responsible for central vision and high visual acuity. These two xanthophylls protect the macula from the damaging photo-oxidative effects of short-wave UV radiation.

Xanthophylls such as zeaxanthin, lutein and cryptoxanthin have been shown to reduce the risk of age related macular degeneration (Moeller, et al., 2000 and Seddon, 1994), demonstrate control over LDL cholesterol (Chopra, et al., 1994), prevent coronary heart diseases (Howard, et al., 1996 and Morris, 1994), scavenge free radicals and enhance immunity (Chew, et al., 1996). Beta-Cryptoxanthin and beta-carotene are also major sources of vitamin A (Wingerath, et al., 1995). Both zeaxanthin and lutein are reported to possess strong anti-tumor properties (Packer, et al., 1999). Epidemiological studies suggest that the antioxidant potential of dietary carotenoids may protect against the oxidative damage that can result in inflammation. A modest increase in dietary carotenoid intake is associated with a reduced risk of developing inflammatory disorders such as rheumatoid arthritis (Pattison, et al., 2005). Zeaxanthin and lutein cannot be synthesized by humans and animals, so these carotenoids must be obtained through the ingestion of food and/or dietary supplements.

Age-related Macular Degeneration (AMD) is the leading cause of blindness for people older than 65 in the United States, and is expected to affect 40 million U.S. residents by the year 2030 (Abel, 2004). Treatments to ameliorate the effects of the disease and methods for preventing the onset of the disease are desperately needed. Since lutein and zeaxanthin play a critical role in the protection of the macula, it is important that people have access to these compounds, either through dietary sources, through supplements, or through so-called functional foods that contain enhanced levels of these nutrients. Numerous epidemiological studies suggest that the typical intake of lutein and zeaxanthin is only in the 1-3 mg/day range, see Brown et al. (1999) and Lyle et al. (1999). Seddon et al. (1994) reported a relationship between the intake of lutein and zeaxanthin at 6 mg per day and a decreased risk of AMD and cataracts. This dietary gap of 3-5 mg per day can be eliminated with the use of supplements.

A higher dietary intake of carotenoids is also associated with a lower risk for AMD (Age-related Macular Degeneration) occurring in older adults. Hereditary forms with an early onset include Stargardts, Best's Disease and progressive Cone Dystrophy. Hereditary retinal degenerations that attack the whole of the retina tend to be more severe. The most common types of these diseases are Retinitis Pigmentosa, Choroideremia, Ushers Syndrome and diabetic retinopathy. Individuals consuming the highest levels of carotenoids exhibit a 43% (statistically significant) lower risk for AMD (Seddon, et al., 1994). The specific carotenoids, zeaxanthin and lutein, are most strongly associated with a reduced risk for AMD. Zeaxanthin and lutein are the sole xanthophyll pigments found in the retina and concentrated in the macula. Excellent reviews of the role of carotenoids in the macula are found in Davies, et al., (2004), Stahl, et al., (2005), Stringham, et al., (2005), Ahmed, et al., (2005), Stahl, (2005), Beatty, et al., (2004), Davies, (2004) and Alves-Rodrigues, (2004).

There is a strong association between higher consumption of dark green vegetables, which contain xanthophylls, including zeaxanthin and lutein, and a decreased risk for light-induced oxidative eye damage, such as cataract formation, see Brown, et al. (1999) and Ribaya-Mercado, (2004). Although dark green vegetables are an excellent dietary source of zeaxanthin and lutein, the isolation and purification of these compounds in large quantities from green vegetables is time-consuming and costly. Twenty-five grams of a fresh, dark green vegetable such as kale theoretically provide 10 mg of lutein (Khachik, et al., 1995). Corn, one of the highest plant sources of zeaxanthin, contains about 0.528 mg of zeaxanthin per 100 grams of corn (Lutein and Zeaxanthin Scientific Review, Roche Vitamins Technical Publication HHN-138210800). It would require 1.9 kg of corn or 0.623 kg of peppers to provide 10 mg of zeaxanthin from these sources.

Therefore, a highly concentrated source of natural zeaxanthin is needed for the manufacture of dietary supplements and functional foods. Moreover, zeaxanthin is an important ingredient to add color to foods and as an additive in animal feeds to color poultry skin, egg yolks, fish flesh and the like. A natural source of zeaxanthin that can be used in foods is preferred and/or regulated over a synthetic product in these applications.

Cis-trans Forms and Stereoisomers

Zeaxanthin from natural sources is generally obtained in the form of an all-trans isomer. It is well known that the trans isomer can be converted to cis forms by the application of heat and/or light or by the addition of a catalytic amount of iodine [(Zechmeister, (1962); Khachik, et al., (1992); Updike, et al., (2003); Englert, et al. (1991) and references therein; Karrer and Jucker, (1950)]. Zechmeister also discusses isomerization by acid catalysts, contact with active surfaces, via boron trifluoride complexes and biostereoisomerization. Given the number of double bonds in the structure, a large number of different cis isomers are possible. Both cis and trans isomers have been detected in the human retina, but it is thought that the all-trans form is the desired isomer for providing protection to eye tissues. An excellent review of cis-trans isomerization of carotenoids is given by Schieber and Carle (2005).

Zeaxanthin also exists in two enantiomeric and one meso form, namely 3R,3'R; 3S,3'5 and 3R,3'S (note 3S,3'R is identical to 3R,3'S). All three stereoisomers have been found in the human retina (Howard, et al., U.S. Pat. No. 6,329,432), but the 3R,3'R isomer is dominant. It is difficult to separate these three isomers of zeaxanthin from each other in commercial quantities for human consumption. Therefore, for synthetic production of zeaxanthin, either a chiral process or a chiral separation process is needed in order to purify and produce the 3R, 3'R stereoisomer.

Zeaxanthin Needs in the Marketplace

There is a perceived need in the marketplace for naturally derived zeaxanthin, as opposed to synthetic zeaxanthin, that can serve as a dietary source in the form of a dietary supplement, a food or beverage additive, or a food or beverage colorant. Furthermore, there is a need for zeaxanthin for dietary supplements, food or beverage additives, and food or beverage colorants in biologically available forms.

There is also a need for naturally derived zeaxanthin, as opposed to synthetic zeaxanthin, that can serve as an additive in animal feeds, such as poultry feed, to color flesh and skin, egg yolks and fish flesh. Certain types of poultry feed additives prepared from corn gluten contain a relatively high percentage of zeaxanthin (about 15-30%), when measured as a percentage of total carotenoids. However, the total carotenoid content of these feed additives is very low (only about 100 milligrams of total carotenoids per pound of poultry feed). Another type of poultry feed additive is prepared from marigold extracts. This additive contains roughly 100-200 times as much yellow pigment per pound of additive (i.e., about 10 to 20 grams of lutein and zeaxanthin per pound); however, more than 95% of the yellow pigment in this marigold preparation is lutein, not zeaxanthin. Zeaxanthin comprises only about 2 to 5% of the yellow pigment in this poultry feed additive (Garnett, et al., U.S. Pat. No. RE 38,009).

Plant Sources of Zeaxanthin

The public generally prefers to consume compounds that are derived from natural sources as opposed to those that are produced synthetically. Natural sources containing high levels of zeaxanthin currently include certain mutant varieties of marigold flower petals, berries of the genus *Lycium* and *Physalis*, and specifically Chinese wolfberries (*Lycium chinense*). Preferred materials containing zeaxanthin include fruits like oranges, peaches, papayas, prunes, and mangos (Levy, U.S. Pat. No. 6,191,293). Todd, et al., (U.S. Application Publication No. 2006/0185034) describe a *Capsicum* plant that expresses very high levels of zeaxanthin; hereafter known as "orange paprika" or the oleoresin derived from it as, "Todd et al. *Capsicum* oleoresin". Todd, et al. describe the dried ripe fruit pod flesh as containing greater than 0.4% zeaxanthin, as measured as the free-form of zeaxanthin, and exhibiting a percentage of zeaxanthin relative to total carotenoids of greater than 50%.

While the present invention is directed in particular to the saponification of zeaxanthin esters extracted from *Capsicum* and isolation of free-form zeaxanthin in high yield and state of purity, one skilled in the art would be able to apply these teachings to zeaxanthin from other sources and to other xanthophyll derivatives obtained from a variety of sources. Other xanthophylls which may be saponified/isolated according to the present invention include lutein, beta-cryptoxanthin, capsanthin, capsorubin, antheraxanthin, violaxanthin, and the like.

Beta-carotene and other carotenoids are desirable materials to isolate for nutraceutical applications since it is reported they quench active oxygen species such as singlet oxygen without damage to themselves. They can do this repeatedly, converting singlet oxygen back to ground state oxygen, thereby preventing singlet oxygen from causing damage, which damage may lead to cancer, including skin or lung cancer. Beta-carotene is also a very efficient free-radical trap (Biyani, et al., 2000). The methods for saponifying and isolating xanthophyll esters of the present invention may be used to isolate carotenes which may be present with the xanthophylls in a purified form.

Saponification

Zeaxanthin from natural sources usually exists as a mixture of free xanthophyll compounds together with the pigment in the form of mixtures of mono and diesters of fatty acids. The fatty acids generally contain from eight to twenty carbon atoms. Zeaxanthin of *Capsicum*, typically is a mixture of these three forms in combination with fatty acids such as include linoleic, palmitic, oleic, linolenic, myristic, stearic, lauric, and the like.

Many methods for converting these esterified forms of zeaxanthin to their free alcohol forms are known and documented. Methods for preparing esters from the non-esterified form are also known and documented. Saponification is the conversion of the fatty acid ester into alcohols and the alkali salts of the fatty acids (soaps) by treatment with a base such as sodium or potassium hydroxide. After saponification, xanthophylls are often further purified by recrystallization and/or chromatographic techniques.

Zelkha, et al., (U.S. Pat. No. 6,797,303) teach a process for extracting plant matter. Zelkha, et al. teach that one should first wash plant matter, such as Chinese wolfberries, with water to lower the Brix of the aqueous phase to less than or equal to 10° Brix, before milling and separation of the remaining plant matter (pulp) by decanting or centrifuging, and prior to extraction of the pulp with an organic solvent to create an oleoresin. Zelkha, et al. teach that when unwashed plant matter having a Brix greater than 10° is extracted, the subsequent separation of the pulp from the extracting solvent is problematic due to generation of three phases which are difficult to separate, when the plant material before extraction is not dried, and the resulting oleoresin is of poor quality, low content of the desired lipophilic substance, i.e. carotenoids and is unsuitable for use for further isolation of the carotenoid contained therein.

Zelkha, et al., report a process for extracting carotenoids from plant matter, whose Brix is greater than 10° and making an oleoresin from that extract. Their process focuses on getting the Brix below 10° prior to solvent extraction. During this process, they saponify the oleoresin derived from washed wolfberry plant material having less than 10° Brix, to liberate the free form of the zeaxanthin. The saponification reaction of Zelkha, et al., is carried out at a temperature of 70° C. to 80° C. in a mixture containing an aqueous solution of potassium hydroxide, ethanol and hexane for about 1 hour. Upon hydrolysis of the zeaxanthin diester-containing oleoresin, zeaxanthin crystals precipitated and the mixture was filtered. The solid fraction contained about 70-90% zeaxanthin, but no yield was given. No further detail was given, no further purification was described.

The process of the present invention starts with oleoresin that has not been subjected to the pre-extraction procedures taught by Zelkha, et al. and while it also uses aqueous potassium hydroxide, an alcohol and a low boiling hydrocarbon, there are other important differences. First, in the instant process the starting material is derived from paprika pods and not Chinese wolfberries. Further, the instant process is suitable for saponifying oleoresins that contain relatively low levels of xanthophyll esters. The Zelkha et al. process does not contain sufficient purification steps to achieve high levels of purity from these kinds of oleoresins. Second, the zeaxanthin yields (up to 80%) and purity (up to 70%) in the instant process are very sensitive to the workup conditions, and it is these workup processes that are the subject of this disclosure. Reactions 24 through 27 in Example 1 of the instant invention give representative yields and purities that were obtained by running a similar saponification procedure to that described by Zelkha, et al. on *Capsicum* oleoresin. Yields ranged from 45% to 65% with purities ranging from 9.2% to 20.1%. It should be noted that the 20.1% purity material was obtained in only 45% yield.

Ausich, et al., (U.S. Pat. No. 5,648,564) describe a method for producing xanthophyll crystals using propylene glycol and aqueous alkali, which crystals are free of trapped solvents. Ausich, et al. teach a method of forming xanthophyll crystals without the use of relatively toxic organic solvents during isolation or crystallization. Furthermore, Ausich, et al. teach that wolfberries (*Lycium barbarum*) are an excellent source of zeaxanthin, and use solvent free zeaxanthin oleoresin derived from wolfberries as starting material for saponification and crystallization using propylene glycol and aqueous alkali. No yield or purity of zeaxanthin is reported in the example for the extraction, isolation and purification of zeaxanthin from wolfberries. Ausich, et al. report that for lutein oleoresin derived from marigold flowers (*Tagetes erecta*), 59 percent of the total carotenoids were recovered from the starting oleoresin, and that 93.1 percent of the carotenoids were lutein. Ausich, et al. mention that similar manipulations using an oleoresin from dried red peppers of *Capsicum annuum* in place of the ground marigold flower petal oleoresin provides a mixture of capsanthin and capsorubin crystals; however, no data regarding yield or purity of capsanthin and capsorubin is provided.

For purposes of comparison, the (Ausich, et al.) process was performed using zeaxanthin oleoresin obtained from *Capsicum* extraction, and although the reaction went to completion (>99% HPLC yield of free form zeaxanthin), the isolated free-form zeaxanthin was obtained in only 54.6% yield and 31.6% purity.

Grant, et al., (U.S. Pat. No. 3,523,138) teach a method of making a xanthophyll product from marigold flowers by contacting marigold petals or an oily extract of marigold petals with an alkali in water and with alcohol at reflux for up to 24 hours to saponify the lutein diesters, thus liberating free lutein. The resulting lutein was separated by extraction from the reaction mixture with an organic solvent such as isopropyl ether, chloroform or ether. The organic solution was then evaporated to obtain a solid containing the free lutein.

These workers did not use the isolation procedures described in the instant invention. Their source of xanthophylls is limited to marigold only, and it has been shown that the source of xanthophylls is important with respect to how the material will respond to a given saponification and xanthophyll isolation procedure. They further do the saponification in water, alkali and an alcohol such as methanol or ethanol. They do not use a hydrocarbon in the saponification reaction itself, which has been shown to be advantageous in the process of the present invention. They also teach neutralization of the saponification reaction mixture, which has been shown to be problematic for xanthophyll recovery and purity in the current invention. Grant, et al., also teach extraction of lutein with an ether or chloroform, which solvents are not used in the process of the present invention.

Khachik, (U.S. Pat. No. 5,382,714) describes a method for the isolation, purification and recrystallization of lutein starting with saponified marigold oleoresin, which contains free lutein. The saponified marigold oleoresin was prepared by treating an organic solvent extraction of dried marigold flowers (*Tagetes erecta*) with an alkaline solution at 65° C. until greater than 98% of the lutein existed in the free form. The product was then homogenized with distilled water and ethanol (2.3:1 volume ratio) at room temperature for 30 minutes. The mixture was filtered and the filtrate discarded. The isolated orange precipitate was washed with distilled water until the filtrate was nearly colorless and the pH was neutral. The precipitate was then washed sequentially with cold (0° C. to 5° C.) ethanol and hexane, respectively. The resulting lutein was 70% pure by spectroscopic analysis, but no yield was reported or is calculable. Final purification was accomplished by recrystallization from a 1:1 mixture of dichloromethane and n-hexane. The solution was kept cold −20° C. to −10° C. for 3 hours. The resulting crystals were then filtered and washed with cold n-hexane (0° C.) and dried under vacuum. The purity was greater than 97%. A yield is not reported for this process. While high purity is important, to run a commercially viable and successful process, one must have high yield as well.

When a similar process was used for the Todd et al. *Capsicum* oleoresin, such as reactions #1-13 in Example 1, lower purities and yields were obtained. The highest purity obtained was 31.7% and the corresponding yield was 45%. Hexane was needed during the saponification to obtain higher yields and purities. Additionally, it was shown with the process of the present invention, that only two water washes could be done, because a third wash resulted in a persistent emulsion, which made further workup extremely difficult. The process described in the instant invention provides yields of from 60 to 80%, of materials suitable in purity for use in beadlet manufacture and nearly quantitative recovery of all input xanthophylls, whose fractions have differing states of purity. The reaction yields for liberation of zeaxanthin from its esterified form is typically >99% and isolated yields of free-form zeaxanthin from the saponification reaction are about 60 to 80% corresponding to >99% of input all-trans-zeaxanthin. An additional 10 to 20% of zeaxanthin is recoverable by precipitation on standing from the methanol supernatant with a purity of 2 to 20%. The remaining 10 to 20% yield is recoverable from the methanol supernatant by desolventization, but its purity is only about 1 to 2% and it contains an abundance of cis-isomers.

Khachik, (U.S. Pat. No. 6,262,284) describes a process for liberating zeaxanthin from its esterified form from Chinese wolfberries using tetrahydrofuran (THF), an alcohol and 5% or 10% potassium or sodium hydroxide, maintained at pH=12 for 1 to 2 hours at room temperature. In the first example of Khachik, the free zeaxanthin was isolated by filtering the reaction mixture and it is stated that the solids formed were washed with tetrahydrofuran. The solvents were evaporated under reduced pressure and the solids were stirred with water and ethanol. The mixture was then centrifuged and the solids washed two more times so that the pH of the aqueous wash was pH 7. The solids were then washed with ethanol, centrifuged and dried under vacuum to give orange crystals containing 75% zeaxanthin. Silica gel treatment was also listed as an option for increasing the purity of the 75% zeaxanthin to 97%. Lastly, the zeaxanthin could be recrystallized from THF and water to provide zeaxanthin in purities up to 97% or greater. One drawback of the Khachik process is that it uses tetrahydrofuran, which is an ether that readily forms peroxides. Although Khachik states that THF is "quite safe for commercial production", it can present a dangerous explosion hazard on a production scale. Another drawback of the Khachik process is the expense associated with the use of a silica gel process step. In addition, since no yields were reported or calculable from the data presented, it is difficult to gauge the industrial feasibility of the Khachik process.

Kimura, et al. (1990) report on the saponification of synthetic carotenoids and natural carotenoids in food samples (tomato, kale, papaya) using different procedures. They report that conflicting results exist in the literature on the stability of carotenoids to saponification and the purpose of their study was to resolve those conflicts. Kimura, et al. reported that hot saponification resulted in greater losses of carotenoids, together with the formation of cis isomers and epoxycarotenoid byproducts as well. Kimura, et al. also note that degradation of carotenoids was further aggravated by contact between the carotenoids and the alkali.

Kimura, et al. teach that using petroleum ether makes the saponification conditions less harsh due to temperature reduction and a protective effect on the released carotenoids. They also reported that carotenes were more stable than xanthophylls to saponification. Running the saponification in alcohol vs. an alcohol and alkane mixture gave higher percentage losses of beta-carotene. However, the conditions such as alcohol type (methanol vs. ethanol), base concentration (10% vs. 60%), and times were not identical in the comparison of the with- and without-petroleum ether cases. This makes a direct comparison difficult.

We have not observed this phenomenon and have stability data that demonstrates that zeaxanthin is stable in aqueous methanolic potassium hydroxide for at least 15 days with no loss in zeaxanthin content or decrease in trans:cis ratios (see Example 2). Kimura, et al. further report that saponification of carotenoids at room temperature in petroleum ether for 16 hr, with an equal volume of 10% methanolic potassium hydroxide was the preferred method for retaining beta-carotene, gamma-carotene, beta-apo-8-carotenal and lycopene; however, even under these mild conditions, lutein, zeaxanthin and violaxanthin from kale degraded significantly. Kimura, et al. noted that these losses could be reduced to insignificant levels by using an atmosphere of nitrogen or an antioxidant. Kimura, et al. report the levels of zeaxanthin as means and standard deviations of duplicate determinations using this method of cold overnight saponification of the zeaxanthin composition of kale, as shown in Table 1.

TABLE 1

Levels of zeaxanthin (ug/g) in kale.

| Carotenoid | Unsaponified | Saponified | Saponified under Nitrogen | Saponified with pyrogallol |
|---|---|---|---|---|
| Zeaxanthin | 4.4 +/− 0.7* | 1.8 +/− 0.1** | 2.2 +/− 0.3* | 1.9 +/− 0.0* |

The values in the row having the same superscript were reported as not significantly different ($p \leq 0.05$). It is not stated, but presumed that the concentrations reported are calculated back to the concentration that would have been in the plant material. However, for duplicate measurements, the confidence intervals are extremely large, and this "significant" difference can be misleading. If these means and the standard deviations remained the same for more replicates, they would be considered significantly different by Tukey's test. It appears that on an absolute basis, that there is very little difference between the saponified, the saponified under nitrogen and the saponified with pyrogallol results within one standard deviation. There appears to be about a 50% loss between the unsaponified material and the saponified materials in general.

Using the method of the present invention and *Capsicum* starting material, a completely different result is obtained. We observe <1% loss of zeaxanthin and furthermore we observed an increase in the amount of the trans isomer to that of cis isomers.

Granado, et al. (2001) describe the comparison of two analytical procedures for the preparation of xanthophyll samples for HPLC and UV-VIS analysis. Granado, et al. describe saponification reactions in ethanol with pyrogallol, 40% potassium hydroxide under nitrogen and in the dark. The workups include partitioning between water and dichloromethane/hexane in one case vs. water and diethyl ether/petroleum ether. The two methods were found to give equivalent analytical results. Granado, et al. do not teach a process suitable for isolating free zeaxanthin on a commercial scale, rather Granado, et al. teach a sample preparation for an analytical method.

Montoya-Olvera, et al., (U.S. Pat. No. 6,504,067) describe an industrial process to obtain xanthophyll concentrates of high purity from plant extracts comprising: refining the plant extracts by treating them with a diluted alkali, followed by treating them with a diluted organic acid or inorganic acid in order to eliminate impurities and obtain a refined extract. The refined extract was saponified by means of a strong alkali aqueous solution at 90° C. under nitrogen, treating the saponified mass with a dilute organic or inorganic acid, followed by several water rinses to a neutral pH in order to separate a xanthophyll concentrate and finally removing any remaining impurities by extracting with hexane. These final steps produce a concentrate that is >95% xanthophylls with 94.5% recovery of the original xanthophylls.

Montoya-Olvera, et al., teach that the acidity, or acid value, of the input oleoresin and the acid:alkali ratio used in the pretreatment step is a key parameter for the process. However, Montoya-Olvera, et al. do not teach how to determine the acid value, and accepted methods (such as AOAC, ASTA, Food Chemical Codex) for determining acidity of an oil are based on titration using a phenolphthalein indicator, which is extremely difficult to visualize in solution with a dark red or orange oleoresin. Montoya-Olvera, et al. teach that capsanthin and capsorubin concentrates may be obtained when *Capsicum* is used as the starting material, although no specific examples are provided, which examples may have demonstrated how the acid value may be measured in a dark red or orange oleoresin; moreover, no data regarding yield and purity is given. Montoya-Olvera, et al. teach that lutein and zeaxanthin concentrates are obtained when Tagetes oleoresin is used as the starting material and provide examples for the isolation of such concentrates which are derived specifically from Tagetes plant material.

When applied to Todd et al. *Capsicum* oleoresin, this process fails at the very first step, in that we were unable to achieve a separation even after centrifuging for 6 hours (See Example 10). Even if it was possible to carry out the process on *Capsicum* oleoresin, the Montoya-Olvera, et al. process is clearly different from that described in the present application in that we use lower temperatures and a hydrocarbon solvent in our reaction to help improve the purities and yields of our final product.

Bhaskaran, et al., (U.S. Pat. No. 7,179,930) teach a process to saponify xanthophylls using phase transfer catalysts in an alcoholic medium. Examples of these phase transfer catalysts are quaternary phosphonium salts and quaternary ammonium salts.

Madhavi, et al., (U.S. Pat. No. 6,380,442) teach a process to isolate carotenoids, especially lutein, from a lutein source, such as marigold oleoresin, using isopropyl alcohol, water and alkali, for a minimum of 60 to 90 minutes at a temperature of about 60° C. to 65° C. The hydrolyzed carotenoids were precipitated from the reaction mixture by addition of water and the precipitate was recovered by centrifugation, followed by repeated water washings and a drying step to provide a fine crystalline material. Madhavi, et al. teach a process for isolating carotenoids from marigold oleoresin, the preferred starting material, with minimal use of organic solvents. The process is not attractive for commercial applications because the water required is more than 30 times per kilogram the input material.

A similar process was performed using *Capsicum* oleoresin containing 2.7% zeaxanthin present mainly in its esterified form, using 45% potassium hydroxide in isopropyl alcohol, wherein heptane was also added to the reaction mixture. The resulting free-form zeaxanthin product had a purity of 2.9%, with a corresponding isolated zeaxanthin yield of 48% (See Example 23). Typically adding a hydrocarbon solvent with an alcohol provided higher yields and purities than the case where no hydrocarbon was added with the Todd et al. *Capsicum* (See Example 1).

Kumar, et al., (U.S. Pat. No. 6,743,953) describe a process for the isolation of high purity xanthophyll crystals (at least 85% total xanthophylls, and at least 90% trans lutein and/or zeaxanthin) which comprises admixing and heating xanthophyll ester concentrate with excess alcoholic alkali solution, maintaining the resulting mixture at a temperature in the range of 65° C. to about 80° C., for a period sufficient to saponify the xanthophyll esters, removing the aliphatic alcohol from the mixture under reduced pressure to obtain the crude saponified concentrate. The crude mixture was then admixed with water at room temperature to form an oily mixture, which was extracted with ethyl acetate three times to produce a xanthophyll extract, which was washed two times with water. The ethyl acetate was distilled off under reduced pressure to recover ethyl acetate and to produce the xanthophyll concentrate. The concentrate was then admixed with a solvent or mixture of solvents, preferably acetone and hexane at room temperature with stirring. The xanthophylls separated out as crude crystals and were removed by filtration. Finally the crude crystals were further purified by washing with an aliphatic alcohol and vacuum dried to obtain xanthophyll crystals that were at least 85% xanthophylls by weight and greater than 90% trans lutein by HPLC. The disadvantages of the Kumar, et al. process are the low isolated yields (see Table 2), multiple distillation steps, the multiple washing steps, and the crystallizing, filtering and vacuum drying steps. These are costly steps in a commercial process and make the process inefficient and unlikely to be cost effective.

TABLE 2

Reported inputs and outputs and yields thereby calculated from Kumar, et al., (U.S. Pat. No. 6,743,953).

| example# | reported inputs | | reported outputs | | calculated yield |
|---|---|---|---|---|---|
| | mass | % xanthophylls | mass | % xanthophylls | |
| 1 | 57.98 | 11.54% | 1.98 | 86.23% | 26% |
| 2 | 56.3 | 11.82% | 1.93 | 88.69% | 26% |
| 3 | 51.6 | 11.82% | 2.11 | 90.07% | 31% |
| 4 | 50 | 11.82% | 2.11 | 90.21% | 32% |
| 5 | 47.3 | 11.82% | 1.52 | 91.34% | 25% |
| 6 | 50.4 | 11.82% | 2.299 | 89.05% | 34% |
| 7 | 51.6 | 11.82% | 1.996 | 85.73% | 28% |
| 8 | 47.3 | 11.82% | 1.73 | 81.41% | 25% |
| 9 | 50 | 11.82% | 2.78 | 90.58% | 43% |
| | | | | | 30% <-- average |

In addition, the relatively low solubility of zeaxanthin in ethyl acetate (ca. 1.07 gram/liter; see Example 11) equates to a relatively small amount of oleoresin that can be converted to free-form zeaxanthin in any given vessel, when compared to the process described in the instant invention. For example, it would require more than 1000 gallons of ethyl acetate to dissolve 10 pounds of zeaxanthin whereas in the instant invention (see Example 6), approximately 10 pounds of zeaxanthin, present in the input oleoresin predominately in esterified form, were saponified in a 400 gallon vessel. To run the same amount of oleoresin using the process described in Kumar, et al. would require a much larger vessel and which may limit the use of the Kumar process for industrial scale purification of zeaxanthin.

Tyczkowski and Hamilton (1990) describe the extraction of free form lutein from a commercial source of saponified lutein and the further crystallization of that extract to produce analytically pure standards. The method of Tyczkowski and Hamilton uses a combination of four solvents in the extraction process (hexane:acetone:toluene:absolute ethanol in a 10:7:7:6 vol/vol/vol/vol ratio). Toluene is a known teratogen and ethanol is a controlled substance. These two factors alone make this an impractical method for a commercial process to purify lutein. Recycling of such a complex solvent mixture on a large production scale also presents costly challenges. The procedure further involves low temperature (4° C.) crystallization to produce the final product. Low temperature crystallization is also a costly procedure.

Sas, et al., (U.S. Pat. No. 5,876,782) teach a method of treating natural plant material in situ using alcohol and a base capable of transesterifying the esters of xanthophylls such that free form xanthophylls were formed as well as the esters of the fatty acids. The reaction was neutralized with acid and solvent removed by drying. The resulting solid was then isolated as the product. Sas, et al. further describe that the process does not involve the use of an aqueous solution, but instead, use an alcohol in situ. Sas, et al. teach the use of neutralization with acid, which has been shown to be problematic in the process of the present invention. Additionally, the Sas, et al. process has no additional steps, such as washing or partitioning, to increase purity and purities were not reported for their isolated products.

Transesterification forms esters of the fatty acids, rather than the salts of the fatty acids. This is a different process than saponification, and as such would imply differences in the workup and isolation of product. Sas, et al. even state that their invention "does not require the organic extraction step, nor the saponification step, to provide an improved plant material." Thus, Sas, et al. recognized that the processes are different.

Sas, et al. provide an example for the liberation of capsanthin from red paprika. No yields were reported. Since the subject of the Sas, et al. disclosure is the conversion of esterified to free-form xanthophylls in situ in plant material, the concept of 'purity' is not addressed.

Sas, et al. do not describe the method of the present invention; the highest purity of zeaxanthin achieved from transesterification reactions using methanol and sodium methoxide was 45.8%, with a yield of 58% (See Example 1).

Sas, et al., (U.S. Pat. No. 6,221,417) describe a human food colorant composition and a process obtaining such food colorant composition. Sas, et al. convert the esterified forms of xanthophylls to free-form xanthophylls via transesterification using a base such as potassium hydroxide at pH=11 to 14, in dry methanol for 10 hrs at 69° C. The resulting mixture was neutralized with phosphoric acid after which the solvent was removed via distillation over 16 hours at 69° C. The residue was dried at room temperature or via vacuum drying at a temperature less than 50° C. Sas, et al. provide an example for the liberation of capsanthin from red paprika. No yields are reported. Since the subject of the Sas, et al. disclosure is the conversion of esterified to free-form xanthophylls in situ in plant material for a food colorant, the concept of 'purity' is not addressed. An indication of the range of purities obtainable by this procedure is summarized in Sas, et al., "a fine powder with a xanthophyll activity of 10-14 g/kg is obtained". The fine powder isolated via the process described in the instant invention has at least 50 times greater 'xanthophyll activity'.

Rodriguez-Bernaldo de Quiros and Costa (2006) analyze and review carotenoid compositions found in vegetable material and human plasma. Rodriguez-Bernaldo de Quiros and Costa discuss issues with saponification of xanthophylls and provide several references indicating that xanthophyll recovery is very sensitive to temperature and reaction conditions.

Khachik, et al., (1986) report an important loss in the xanthophyll content of raw broccoli after applying a treatment of 30% methanolic potassium hydroxide under nitrogen atmosphere during 3 hr, however the loss of carotenes was not significant. This understanding in the art with regard to xanthophyll loss related to saponification is supported by the teaching of Granado, et al., (1992) who also report a loss in the concentration of xanthophylls related to saponification. Furthermore, Scott, et al., (1992) state that "Depending on the nature of the carotenoid, saponification may result in destruction or structural modification."

This makes the resulting reaction yields from the process of the present invention all the more surprising. There is no significant loss in xanthophylls using 45% potassium hydroxide under reflux for up to 40 hr (see Example 3) nor was any significant loss of zeaxanthin observed after allowing the mixture to sit in strongly basic (pH~14) solution at room temperature for 15 days (Example 2). In fact, we further see an increase of the more highly-desired trans isomer via isomerization of the cis isomer of zeaxanthin under these conditions.

Hart and Scott, (1995) employed mild saponification conditions to fruits and certain vegetables, like peppers, in a process using methanolic potassium hydroxide (10%) under nitrogen, in the dark for 1 hr at room temperature. Hart and Scott found that these mild conditions gave the maximum values for the carotenoids of interest. Hart and Scott further teach that for higher fat content materials, a higher concentration of potassium hydroxide is required.

Larsen and Christensen (2005) describe an analytical method for carotenoid analysis that uses a strongly basic resin to gently saponify the chlorophyll and carotenoids present in leafy green vegetables. This saponification involves the use of an acetone extract of the leafy material followed by treatment with base for 30 minutes followed by filtration. The initial concentration of the carotenoids in the samples submitted to saponification were between about 0.0002% to 0.0023%, which carotenoids were further reduced in concentration during the saponification step. This is fine for an analytical procedure, but a very low concentration for a commercial process. The concentrations achieved in the process of the present invention are about 200 to 2000 times greater than the Larsen and Christensen procedure. Larsen and Christensen discuss the method of Khachik, et al., (1986) and observe similar recovery percentages for standard treatment with methanolic potassium hydroxide, and which recovery percentages are lower for all carotenoids, except beta-carotene. Larsen and Christensen attribute the poorer recovery in the Khachik, et al. procedure to longer contact times with hydroxide ions resulting in oxidation and isomerization due to the many laboratory operations involving multiple extractions and evaporations.

Majeed and Murray, (WO 02/060865) teach a process for saponifying and isolating a composite mixture of zeaxanthin, cryptoxanthin, capsanthin, capsorubin and/or beta-carotene from a special variety of chili (Capsicum) known as the Byadagi/Chappatta. The process involves treating an acetone-extract oleoresin made from the Byadagi/Chappatta chili with ethanol and aqueous alkali for 2 to 8 hours at room temperature. The reaction mixture was diluted with 4 parts of a mixture of alcohol and water in a 1:1 ratio. The mixture was extracted with ethyl acetate or toluene or a mixture of the two. The organic layer was washed with water to remove the alkali, and then concentrated to one-third to one-quarter the original volume to initiate crystallization of the zeaxanthin. The crystallization was kept at 0° C. to 5° C. to complete the crystallization, after which it was filtered and dried at 35° C. to 75° C. with high vacuum for 10-48 hours. Majeed and Murray describe using dichloromethane in place of the ethyl acetate and/or toluene extraction solvent above.

We obtained samples of Byadagi/Chappatta chilies (the latter designated S-66) from India, analyzed them for their zeaxanthin content, and compared the results with those of the inventive *Capsicum* cultivar described in Todd et al. (U.S. Application Publication No. 2006/0185034). It should be noted that ASTA values are used as a proxies for molar or weight ratios of pigments. ASIA values are calculated from the absorbance of a solution of the extract at a wavelength of 460 nm. The Todd, et al. *Capsicum* (orange paprika) extract have a maximum absorbance at 454-455 nm. Evidence that the samples of the chilies we obtained were similar to those described by Majeed and Murray comes from the similar levels of color reported as ASTA color values (See Example 23 of Todd, et al. U.S. Application Publication No. 2006/0185034 for method and calculations). The Chappatta chili in Majeed and Murray is reported to have an ASIA value of 125.26. The Chappatta chili we analyzed had an ASIA color value of 125.5. The Byadagi chili in Majeed and Murray is reported to have an ASTA color value of 156.9, while the Byadagi chili we analyzed had an ASIA color value of 213.6. The higher color value in the Byadagi chili we analyzed indicates a higher carotenoid pigment level. If one assumed that all of the absorbance was due to zeaxanthin, one would over-estimate the actual amount of zeaxanthin in the chilies Majeed and Murray used. Analysis of the Byadagi chili gave a total zeaxanthin content of 0.0325% of the dry fruit weight. The percent zeaxanthin to total carotenoids was measured as 6.23%. Analysis of the Chappatta chili gave a total zeaxanthin content of 0.0313% of the dry fruit weight. The percent zeaxanthin to total carotenoids was measured as 7.10%. The weight percent of zeaxanthin in the dried pods of the Byadagi and Chappatta chilies are nowhere near as high as the levels of the Todd et al. *Capsicum*. Likewise, the percent zeaxanthin to total carotenoids values for the Byadagi and Chappatta chilies do not approach the levels of the Todd et al. *Capsicum*. Since only very low levels of zeaxanthin are present in the Byadagi/Chappatta chili, the solubility limitation of zeaxanthin in ethyl acetate (See Example 11) is not a concern in the process of Majeed and Murray. However, when larger amounts of zeaxanthin are being processed, very large volumes of ethyl acetate would be required on an industrial scale due to the relatively low solubility of zeaxanthin in ethyl acetate (about 1 gram/liter). Moreover, the low temperature crystallization of Majeed and Murray is not a cost-effective method for a commercial process of saponifying xanthophylls. A further disadvantage of this procedure is that toluene is a teratogen. Furthermore, ethanol is their preferred alcohol for saponification, but is a regulated substance and the measures taken to insure its' proper use make it costly and difficult to use in a commercial process in the U.S.

Pena, (U.S. Application Publication No. 2007/0161826) describes a process for saponifying oleoresin from marigold and boxthorn berries wherein the oleoresin is saponified with 50% aqueous potassium hydroxide at 103° C., followed by addition of an aqueous sodium chloride solution with stirring. The organic phase was then subjected to multiple sodium chloride and hexane washes, followed by the addition of methanol-water and phosphoric acid to the residual paste, then followed by a second methanol-water wash and subsequently three water washes and filtration. This was followed by another water-ethanol wash to provide a product which was 84.5% total carotenoids representing a yield of 68.7% from a marigold extract. This number of washes would be extremely costly on a large scale and sodium chloride would have a detrimental effect on stainless steel in plant equipment. Pena teach a similar procedure using boxthorn berries (*Lycium chinensis*) to provide a total yield of only 20.6% total carotenoids, 97% of which is zeaxanthin. Again, the cost effectiveness of the Pena process to obtain zeaxanthin is questionable, particularly given the recovery of the total carotenoids. Moreover, in the Pena process, many different solvents are used and these must either be recovered and purified to be used in other processes, or the mixed solvent streams for this process must be kept in their own tanks, putting a burden on inventory. Furthermore, ethanol is a regulated substance and the measures taken to insure its proper use are costly.

Xu, et al., (U.S. Application Publication No. 2007/0032683) describe a process for the isolation and purification of xanthophyll crystals from plant oleoresin using food grade solvents. The plant material Xu, et al. saponified included marigold flowers, kale, spinach, broccoli, corn, with marigolds being preferred. The Xu, et al. process comprises the steps of: saponifying the oleoresin in alcohol with aqueous alkali at a temperature of 40° C. to 85° C. for 3 to 5 hours, and then adjusting the pH to 1 to 7 after cooling. Two to ten volumes of water were then added, followed by 0.5 to 2 volumes of alcohol per weight of plant oleoresin. The temperature was then increased to 40° C. to 85° C. for 0.5 to 2.0 hours, during which time a crystalline precipitate formed. The crystals were recovered by centrifugation, then washed 2 to 3 times with water at 70° C. to 85° C. until the supernatant was colorless. The crystals were then leached with dry ethanol and dried in vacuum or freeze-dried. The Xu, et al. process may yield 80% total xanthophylls with at least 90% trans-lutein or zeaxanthin, depending on the plant material used as starting material.

The disadvantages of the Xu, et al. process using the Todd, et al. *Capsicum* is that attempts to decrease the pH from highly alkaline resulted in precipitation of large amounts of fatty acids and poorly compacted solids, resulting in much lower purities than the instant invention (See Example 9). Moreover, the Xu, et al. process specifically calls for the use of dry ethanol and, as mentioned previously, ethanol is a regulated substance and the measures taken to insure its proper use are much more costly than other solvents.

Sethuraman Swaminathan and Kunhiraman Priya Madavalappil (WO 2006/114794) describe a method for producing carotenoids rich in lutein from marigold flower petals. The process comprising the steps of: ensilage of marigolds, dehydration to obtain a dry meal, pelletization of the meal, solvent extraction of the pelletized meal with hexanes, hydrolysis of carotenoid esters with alkali after homogenizing the oleoresin in absolute alcohol, precipitation of the carotenoid crystals with a water and alcohol mixture, washing the precipitate with hot water to remove soaps and impurities, filtration of carotenoids, and drying to obtain crystals in high purity (>90% carotenoids having a minimum of 90% trans lutein) and high yield (55% to 80% isolated yields). The saponification and purification procedure involves homogenizing the oleoresin with absolute alcohol before adding aqueous alkali and heating at 70° C. to 80° C. for 30 minutes. This process is very different from the process of the present invention in that no alkane is used in the saponification process, furthermore, it is limited to marigolds as a source of carotenoids and we have shown that processes optimized for marigolds do not translate well to the Todd, et al. *Capsicum* (see Example 10 using the method of Montoya-Olvera, et al.). Moreover, the input marigold plant material is subjected to an anaerobic fermentation step to fix and enrich the carotenoids present in the marigold petals. This may provide a very different starting material than solvent extraction of the Todd, et al. *Capsicum*. A further disadvantage of this procedure for use with the Todd et al. *Capsicum* is that yields and purities of zeaxanthin are lower if the reaction is run only in alcohol without addition of an alkane (See Example 1).

Rosales, et al., (U.S. Pat. No. 7,150,890) describe the use of metallic halogenides, such as calcium chloride, magnesium chloride, etc. to precipitate fatty acids after xanthophyll oleoresins have been conventionally saponified with aqueous solutions of potassium hydroxide or sodium hydroxide between 80° C. and 120° C. for one to two hours, which provided a saponified marigold oleoresin containing about 30% xanthophylls, of which 94% was lutein and 6% was zeaxanthin. The precipitation was carried out at 35° C. to 50° C., followed by filtration and washing of the precipitate with a polar solvent such as an alcohol or acetone. The filtrates were combined and evaporated to a obtain a residue that contained 91 to 95% of the original amounts of xanthophylls in about the same proportions as the starting material. In only one of the examples do Rosales, et al. give an absolute purity obtained, which in that case was 90% total xanthophylls by weight. In the Rosales, et al. Process, zinc chloride (a Lewis acid), calcium chloride and magnesium chloride were used as titrants.

The disadvantages of this procedure for use with the Todd et al. *Capsicum* is that Rosales, et al. was working with marigold extract, and they precipitated solids from the supernatant along with lutein. They then extract the solids with acetone or alcohol to isolate the lutein. The purities of zeaxanthin were much lower when attempts were made to titrate the saponification mixture to a neutral or acidic pH (See Example 9) and purities were similar or lower by adding a chelator to try to remove metals, and a persistent emulsion occurred with the addition of calcium acetate (See Example 26).

Hoffman, et al., (U.S. Pat. No. 7,109,361) describe a process for the extraction of lutein and zeaxanthin from alfalfa. The overall yield of the process, reported in Example 1, was about 9%. The Hoffman, et al. process involved saponifying 27 lbs of oleoresin with 13 lbs of 40% aqueous potassium hydroxide at 140° F. for one hour. The pH was checked and adjusted if it was lower than pH 12. Next, 500 lbs of acetone was added to 40 lbs of saponified resin at 100° F., blended, and was subsequently separated into two phases via centrifugation. The acetone layer was evaporated to yield 10 lbs of an oil containing 6% lutein. The oil was mixed with 900 lbs of hexane at room temperature and cooled to −10° F. to induce crystallization. The hexane was removed and the crystals were rinsed with water in a 50:1 ratio, water to solids. The 0.6 lbs of crystals contained 75% lutein, which represented a 9% overall yield from the original amount of lutein in the alfalfa oleoresin. The disadvantages of the Hoffman, et al. process are the high volumes of solvent used for the small amount of lutein obtained and the low overall yield from the alfalfa. Additionally, the low temperature crystallization is a cost-inefficient process on a commercial scale.

Muralidhara, et al., (U.S. Pat. No. 5,602,286) describe a process for the recovery of xanthophylls from corn gluten. The Muralidhara, et al. process includes saponification and isolation steps. The saponification step is described to be a conventional saponification reaction. Muralidhara, et al., saponified with alcohol, specifically ethanol in the examples, and potassium hydroxide with the crude xanthophyll extract at reflux for one hour. The reaction mixture was then filtered and the filtrate was evaporated to obtain the refined xanthophylls (about 52% purity) in 47% yield.

The disadvantages of the Muralidhara, et al. process are that the relatively low yield and low purity of xanthophylls from corn. The reported yield is lower than that of the instant invention (60-80% isolated yields) and the purities were not as high as in the instant invention (50-70% purity). They also do not follow the steps of the process of the present invention. Furthermore, Muralidhara, et al. specifically uses ethanol as the alcohol used in the process. As mentioned previously, ethanol is a costly solvent to use in a commercial process.

Rodriguez, (U.S. Pat. No. 5,973,211) teaches a non-aqueous process for isomerization of lutein to epimers of zeaxanthin. The process includes a step for saponification of an oleoresin in the presence of a non-aqueous glycol, such as propylene glycol and/or glycerine, and sodium or potassium hydroxide with heating to 60° C.-80° C. for 50 minutes to 5 hours under nitrogen. The products of saponification were never isolated, since further steps were employed utilizing more base and higher temperatures to isomerize lutein to zeaxanthin.

Sanroma-Virgili, et al., (U.S. Pat. No. 5,998,678) describe a process for the preparation of free-form zeaxanthin via the saponification and isomerization of free-form lutein or lutein diesters or lutein derivatives where the hydroxyl groups are protected with lower alkyl, lower acyl, fatty acyl or a hydroxyl protector group, with an alkaline reagent (such as potassium hydroxide), a polar solvent or mixture from the group consisting of an ether, a polyhydroxyl alcohol, an ether-alcohol or a combination thereof, and wherein the lutein or lutein derivative is of natural or synthetic origin. The products of saponification were never isolated, since conditions were employed to go beyond saponification and to isomerize lutein to free-form zeaxanthin.

Torres-Cardona, et al. (U.S. Pat. No. 5,523,494) teach a process for the isomerization of lutein to zeaxanthin, which may include saponification of the plant extract material which is derived from marigolds or yellow corn. The process includes the slow addition of a strong alkaline base (such as potassium hydroxide) with a temperature from 25° C. to 180° C. for 5 to 96 hours, under an inert atmosphere to effect the conversion of lutein to free-form zeaxanthin. Although it is not specifically stated, the lutein sources listed would imply that an esterified lutein was the starting material. The intermediate, saponified, lutein was not isolated and characterized, and therefore, no yields are reported.

The Torres-Cardona, et al procedure is different from the method of the instant invention in that the important processing steps necessary to saponify and obtain high yields and purities of zeaxanthin from *Capsicum* extracts are not described.

Bernhard, et al., (U.S. Pat. No. 4,883,887) describe processes to make carotenoid structures synthetically. One sub-process describes using an alkali metal hydroxide or alkaline earth metal hydroxide in water, with an optionally inert solvent (e.g. ethers such as diethyl ether, diisopropyl ether, t-butyl methyl ether, tetrahydrofuran, dioxin and 1,2-dimethoxyethane, saturated and aromatic hydrocarbons such as hexane, cyclohexane, benzene and toluene, and the like) at temperatures from 0° C. to reflux. Bernhard, et al. use a synthetic source as starting material and do not disclose extraction/purification of carotenoids from plant material; a natural plant source is generally a more complex matrix, making separations and purifications more difficult. The ethers are dangerous solvents, in general, owing to their propensity to form explosive peroxides on standing. Great care must be taken when using these solvents industrially on a large scale. Additionally benzene is a known carcinogen and toluene is a teratogen.

Khachik, (U.S. Pat. No. 7,173,145) teaches a process for extracting and saponifying zeaxanthin esters from Chinese wolfberries utilizing tetrahydrofuran, an alcohol, and potassium hydroxide for one hour at room temperature. The solution was treated with aqueous hydrochloric acid to lower the pH to 7.0 to 7.5, after which the tetrahydrofuran and alcohol were distilled off under reduced pressure at 40° C. to 50° C. Hexanes were added and zeaxanthin was crystallized, centrifuged and vacuum dried at 60° C., resulting in a 81.7 yield (based on free-form zeaxanthin). This Khachik process uses ethers, which can be an explosion hazard due to peroxide formation and it also involves neutralization.

Attempts at neutralization immediately after saponification using the current invention on *Capsicum* extracts, resulted in a tremendous amount of precipitate (See Example 9), thereby complicating the isolation of zeaxanthin in high purities.

Minguez-Mosquera and Hornero-Mendez, (1993) describe an analytical method for identifying various carotenoid pigments in red peppers (*Capsicum annuum*). The analytical procedure requires the starting material be saponified. The Minguez-Mosquera and Hornero-Mendez saponifying procedure involves an ether extract solution being shaken with 20% potassium hydroxide in methanol solution for 1 hour. The aqueous phase was removed, and the organic phase was washed several times with water, dried over anhydrous sodium sulfate, and evaporated to dryness under vacuum at a temperature lower than 35° C. Minguez-Mosquera and Hornero-Mendez describe an analytical method for identifying individual carotenoid pigments, which analytical method does not pertain to large scale isolation/purification of carotenoids to obtain high yield and high purity.

This procedure differs from the process of the instant invention, in particular, ether is used as a solvent and the pigment composition in their *Capsicum annuum* red peppers is soluble in the organic phase. In contrast, zeaxanthin precipitates out of the aqueous/alcohol solution in the process of the present invention.

Processes for the saponification of paprika oleoresin to obtain the paprika pigments, the major pigments in the paprika being red pigments, and in particular, capsanthin, as the major carotenoid are described. Osamu, et al., (Japanese Patent Application No. 57-133160) describe the saponification of paprika oleoresin with alkaline water and/or alcohol followed by pH adjustment to acidic conditions with water to form two layers. The oil layer was collected and alcohol was added to it and the pigment was obtained by decantation of the liquid and dried. Osamu, et al., (Japanese Patent Application No. 57-180663) describe saponification of paprika oleoresin with the hydroxide, alcholate or carbonate of an alkali or alkaline earth compound, followed by addition of water, pH adjustment with acid to acidic conditions, and lastly extraction of the solids with an organic solvent such as acetone or ethanol and evaporation of the acetone to produce a paprika pigment. These two methods used pH adjustment to the acidic side, which may result in isolation problems, depending on the starting material, and lead to lower purities and yields of xanthophylls in the current invention. Masahiro, et al., (Japanese Patent Application No. 58-173164) describe a process where saponification was used as part of a larger process, the intent of the larger process is to deodorize paprika. Masahiro, et al. describe saponification of an oleoresin in aqueous solution, separating the solids and drying it prior to adding an organic solvent such as acetone or ethyl acetate to extract the pigment. The acetone extract was then concentrated and the concentrate steam distilled to provide deodorized paprika. Masahiro, et al. further describe that capsanthin was the major carotenoid in the oleoresin they were saponifying.

Curl, (1962 and 1964) describes saponification of red and green bell peppers for countercurrent distribution sample preparation. The peppers were blended with water and magnesium carbonate, then mixed with methanol. Celite 503 was added and the mixture was filtered.

Curl, (1953) describes a method for saponification that involves extracting oranges with diethyl ether and adding an equal volume of 20% potassium hydroxide in methanol to form a homogenous solution. The solution was allowed to stand overnight at room temperature, and was then diluted with water and extracted with ether. The ether layer was washed with water, dried over sodium sulfate and evaporated in vacuo.

The purification of xanthophylls from a saponified extract using a crystallization process is described in Rodriguez, et al. (U.S. Pat. No. 6,329,557). The process comprises the steps of dispersing the saponified extract in water to form a dispersion, mixing the dispersion under conditions such that a portion of any water-soluble compounds dissolves in the water to form an aqueous phase and a residue that is not soluble in water, adjusting the pH to between 1 and 7, preferably to between 5.0 and 6.5, then separating the aqueous phase from the residue, contacting the residue with a non-polar solvent under conditions such that a portion of any lipid-soluble compounds dissolves in the non-polar solvent and a portion of the xanthophylls precipitates from the non-polar solvent to form a precipitate, separating the non-polar solvent from the precipitate, washing the precipitate with a polar solvent such that at least a portion of any remaining chlorophylls dissolves in the polar solvent, and separating the polar solvent from the precipitate to yield a product comprising the xanthophylls at a desired level of purity.

This process differs from the instant process in two ways. The first is that it involves a pH adjustment to acid at a point where zeaxanthin is not soluble and a large volume of fatty acids would precipitate, making zeaxanthin isolation in high purity extremely difficult without further processing steps. The second is that it does not use hexane for the saponification reaction, but uses it for the workup. As will be shown later, one of the keys to achieving high purity zeaxanthin is the addition of an alkane to the saponification reaction at the beginning (see Example 1).

As can be seen from the foregoing analysis, there is a need for a process to convert xanthophyll esters derived from *Capsicum* sources to their free (non-esterified) forms in both high purity and high yield. The existing processes in the public domain, including those discussed above, fail to provide a process for *Capsicum* derived xanthophylls that meet the finished product needs for purity, yield, ease of use, industrial compatibility and cost that are required to make product suitable for the nutritional supplement, food and beverage industries. Moreover, the xanthophyll esters present almost exclusively in the trans form in the natural plant sources are often partially converted to their less valuable and less useful cis forms during extraction and further processing. The increased solubility of the cis forms leads to significant yield losses of xanthophylls, over all. Furthermore, there is a need for a process to re-convert cis product back to the more desired trans form.

DESCRIPTION OF THE INVENTION

What we therefore believe to be comprised by our invention may be summarized inter alia in the following words: a method for converting esterified xanthophylls from *Capsicum* into their non-esterified form, which method provides isolated yields of from 60 to 80% of materials in suitable purity for use in beadlet manufacture. A nearly quantitative recovery of all input xanthophylls can be achieved from isolation of lower purity fractions as described below. Additionally, the yield for liberation of zeaxanthin from its esterified form is typically >99% using this method. Isolated yields of free-form zeaxanthin from the saponification reaction are about 60 to 80% corresponding to >99% of input all-trans-zeaxanthin. An additional 10 to 20% of zeaxanthin is recoverable by precipitation on standing from the methanol supernatant, which exhibits a purity of 2 to 20%. The remaining 10 to 20% yield is recoverable from the methanol supernatant by desolventization, at a purity of about 1 to 2% with an abundance of cis-isomers.

OBJECTS OF THE INVENTION

It is an object of the present invention to provide a process for the isolation of zeaxanthin in high yield and high purity from esterified precursors.

It is a further object of this invention is to provide a process for the preparation of a composition from *Capsicum*. As one particular example according to the instant invention, free-form zeaxanthin is produced from oleoresin prepared from *Capsicum annuum* containing a hyperaccumulation of zeaxanthin.

An additional object of the present invention is to recover carotene hydrocarbons in enriched form from the process described herein.

An additional object of the present invention is to maximize the recovery of all-trans-zeaxanthin in high purity.

An additional objective of the present invention is to maximize the throughput of the process in a batch-style reactor.

Yet additional objects will become apparent hereinafter, and still further objects will be apparent to one skilled in the art.

SUMMARY OF THE INVENTION

What we therefore believe to be comprised by our invention may be summarized inter alia in the following words:

A method for converting esterified xanthophylls from *Capsicum* into their non-esterified form comprising the steps of:
- a) contacting xanthophyll esters in an oleoresin with a hydrocarbon, with an oleoresin to hydrocarbon ratio of 1:0.5 to 1:10 (weight/weight), wherein the hydrocarbon is hexane or a mixture of low boiling hydrocarbons;
- b) adding an alcohol at an oleoresin:alcohol ratio of 1:1 to 1:10 (weight/weight);
- c) adding a base at an oleoresin:base ratio of 10:1 to 1:1 (weight/weight);
- d) applying a blanket of an inert gas, selected from, but not limited to nitrogen and argon;
- e) applying heat, if necessary, to at least 20° C. up to reflux temperature;
- f) allowing the mixture to stir and/or reflux under the inert atmosphere for 0.25 to 120 hrs;
- g) reducing the temperature of the reaction mixture to 0° to 50° C.;
- h) allowing the mixture to settle for 0.1 to 1000 hours;
- i) removing the upper hydrocarbon phase rich in carotenes, including alpha-carotene, beta-carotene, lycopene, and the xanthophyll, beta-cryptoxanthin;
- j) optionally adding more hydrocarbon to the remaining reaction mixture with stirring and repeating steps h) and i);
- k) desolventizing the upper hydrocarbon phase(s) to obtain a carotene concentrate;
- l) adding water, optionally mixed with an alcohol and/or complexing or chelating agent, to the lower phase remaining after hydrocarbon removal, with an oleoresin:water ratio of 1:0.1 to 1:5 (weight/weight), then thoroughly mixing;
- m) allowing the system to settle undisturbed for 0.5 to 1000 hours;
- n) draining the lower aqueous phase (first water wash) rich in soaps and other polar soluble materials;
- o) optionally repeating steps l) through n), one or more times;
- p) adding an alcohol to the mixture, optionally adjusting the water content of the mixture to 1-15%, by alcohol addition and/or concurrent or subsequent distillation;
- q) optionally removing the remaining hydrocarbon via distillation;
- r) separating the solid precipitated xanthophylls from the liquid supernatant by decanting, centrifugation, or filtration;
- s) adding to the solid xanthophylls, a wash solvent, and mixing to form a slurry;
- t) separating the solid xanthophylls from the wash solvent by decanting, filtering, or centrifuging;
- u) optionally repeating steps s) and t) until the required purity is achieved;
- v) removing the solvent(s) and drying;
- w) packaging the dried xanthophylls obtained in the preceding step in an inert environment, selected from vacuum packaging or packaging inerted with nitrogen or argon;
- x) optionally, precipitating more solid xanthophylls from the liquid supernatant generated in steps r) and t) by addition of water and/or allowing the supernatant to stand for one or more days, and isolating the precipitate thereby formed by filtration, centrifugation, and/or decantation;
- y) optionally repeating step x) until no more precipitate is formed; and
- z) optionally desolventizing at step x) to recover the xanthophylls;
- aa) optionally adding an antioxidant to the solid prior to desolventizing at steps v), and/or x), and or z);
- ab) optionally extracting the xanthophylls from the precipitate at steps v), and/or x) and/or z) with a suitable solvent such as methylene chloride prior to desolventization; and
- ac) optionally adding water to the precipitate in step ab) prior to extracting;
- ad) optionally raising the temperature of the mixture to 40° C. to 60° C. after draining the water in step n), and isolating the zeaxanthin rich precipitate layer which forms at the bottom of the vessel; and
- ae) optionally repeating steps z), aa), ab) and/or ac) with the precipitate layer formed in step ad), such a method, wherein the ratio of oleoresin to hydrocarbon is 1:1.5 (weight/weight) in step a), such a method, wherein the ratio of oleoresin to alcohol is 1:3 (weight/weight) in step b), such a method, wherein the alcohol is methanol in step b), such a method, wherein the base is a hydroxide, carbonate, or alkoxide with an alkali or alkaline earth metal counterion in step c), such a method, wherein the ratio of oleoresin to base is a 1:1.2 ratio (weight/weight) of oleoresin:potassium hydroxide, with potassium hydroxide added as a 45% aqueous solution in step c), such a method, wherein the temperature in step e) is 50°-80° C., such a method, wherein the number of hours in step f) is 24 hrs, such a method, wherein the reduced temperature in step g) is 20°-25° C., such a method, wherein the number of hours allowed to settle in step h) is 0.5 hours, such a method, wherein the ratio of oleoresin to water in step l) is 1:1.5 (weight/weight), such a method, wherein the number of hours in step m) is 4 hours, such a method, wherein the water content of the mixture in step p) is 2.8%, such a method, wherein the solvent in step v) or step z) is removed by spray drying, such a method, wherein the solvent in step v) is removed by dilution with water and optionally removing the solvent via distillation, decantation, or centrifugation, prior to drying, such a method, wherein the wash solvent in step s and/or u) is methanol, such a method of, wherein the wash solvent in step s) and/or u) is ethanol, such a method, wherein the wash solvent in step s) and/or u) is an alcohol having 1 to 4 carbons, such a method, wherein the wash solvent is a hydrocarbon, such a method wherein the xanthophyll is zeaxanthin, such a method, wherein the purified carotenoids so obtained are formulated and stabilized in bulk, in the form of powder, beadlets, granules, oil dispersions and/or water dispersions, such a method, wherein a co-product comprises beta-carotene, alpha-carotene, beta-cryptoxanthin or a mixture thereof in step k), such a product obtained by the method comprising zeaxanthin, such a product obtained by the method comprising cryptoxanthin, such a product obtained by the method comprising capsanthin, such a product obtained by the method comprising capsorubin, such a product obtained by the method comprising violaxanthin, such a product obtained by the method comprising lutein.

After employing the sample preparation procedure outlined in EXAMPLE 20 to the starting oleoresin for the experimental examples presented herein, and the HPLC conditions detailed in EXAMPLE 20, a chromatogram similar to that presented was generated.

Figure 2:
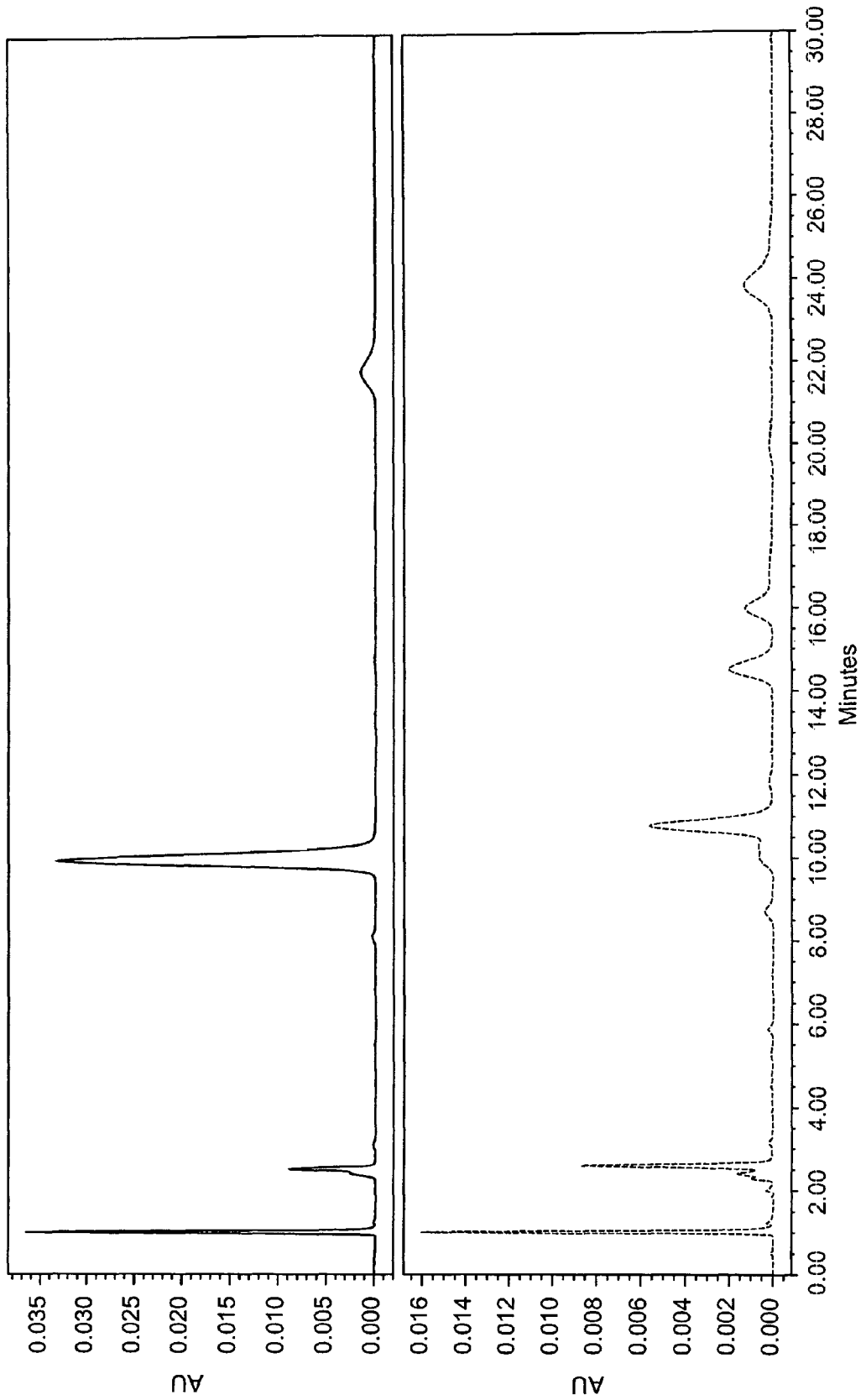

FIG. 2. Determination of zeaxanthin content in experimental saponification products by HPLC.

Typical chromatograms of isolated precipitates (top) and supernatants (below) from experimental saponification reactions. The chromatograms shown are for the corresponding outputs of reaction #17 in the table in Example 1. The large peak eluting around 10 minutes corresponds to all-trans-zeaxanthin. This procedure was used for quantitative determination of zeaxanthin in outputs (solids, supernatants, wash solutions) as well as for determining total reaction yield (HPLC yield).

DETAILED DESCRIPTION OF THE INVENTION

Description of Terms:

As used herein, "orange paprika" or the oleoresin derived from it, "orange paprika oleoresin," are produced from the *Capsicum* plant (or Todd et al. *Capsicum*) described by Todd, et al., (U.S. Application Publication No. 2006/0185034). They describe the dried ripe fruit pod flesh as containing greater than 0.4% zeaxanthin, as measured as the free-form of zeaxanthin and the percentage of zeaxanthin relative to total carotenoids being greater than 50%.

As used herein, "oleoresin" includes resins and volatile oils in a mixture. It includes a liquid or semi liquid preparation extracted (as from *Capsicum*) by means of a solvent, supercritical fluid or mechanical process, and consisting of fixed and/or volatile oils.

As used herein, "crystallizing" includes the process of forming crystals (crystalline material) of a natural product, from solution.

As used herein, "precipitation" includes the process of forming amorphous solids (precipitates) from a liquid solution.

As used herein, "zeaxanthin" refers to a compound having the formula:

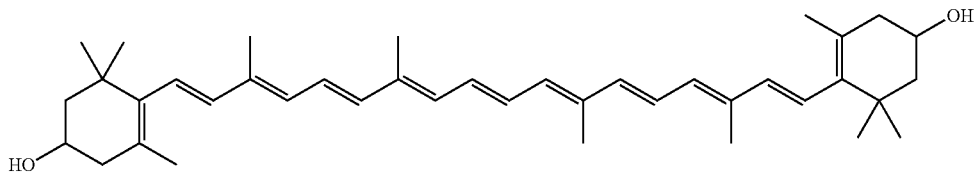

This form with hydroxyl end groups may be referred to as the "free-form" of zeaxanthin. Note that only the all-trans form is shown, but cis isomers may exist as well. One such example is:

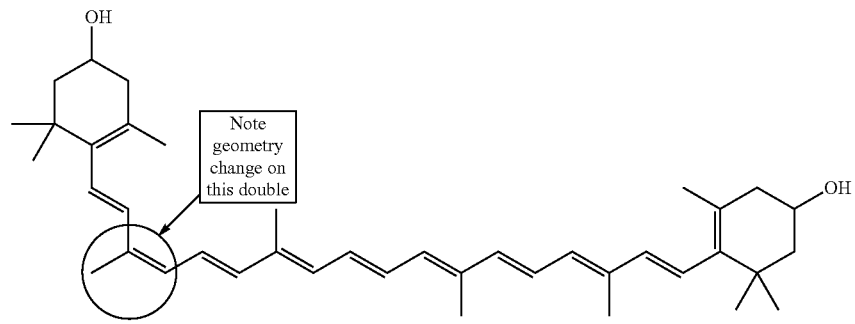

The esterified form of zeaxanthin refers to a compound having the formula:

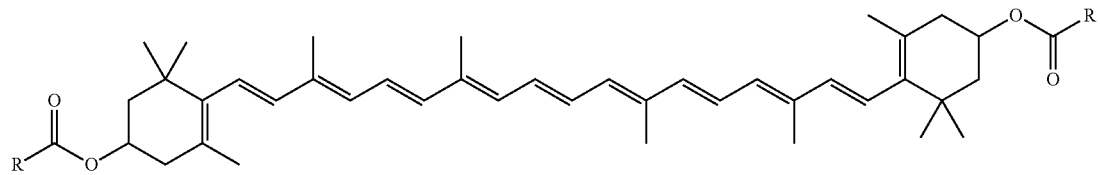

wherein R groups are hydrocarbon radicals typically containing from 7 to 19 carbons. Note that only the all-trans form is shown, but cis isomers may exist as well. As used herein, "all-trans-zeaxanthin" is synonymous with "E-zeaxanthin", i.e. all double bonds are in the trans- or E-orientation. Likewise, "cis-zeaxanthin" is synonymous with "Z-zeaxanthin", i.e. one or more of the double bonds are in the cis- or Z-orientation. Additionally both ends can be esterified (diester) or only one end esterified (mono ester).

As used herein, "lutein" refers to a compound having the formula:

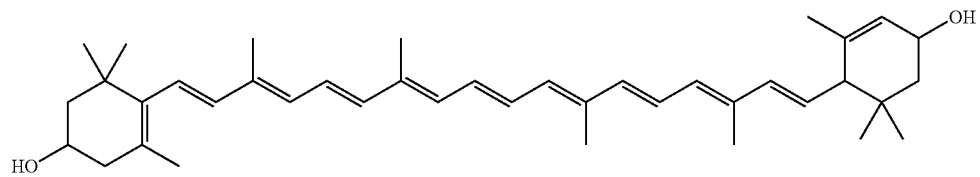

Note that only the all-trans form is shown, but cis isomers may exist as well.

As used herein, "alpha-carotene" refers to a compound having the formula:

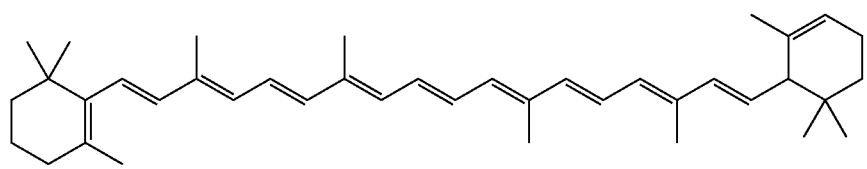

Note that only the all-trans form is shown, but cis isomers may exist as well.

As used herein, "beta-carotene" refers to a compound having the formula:

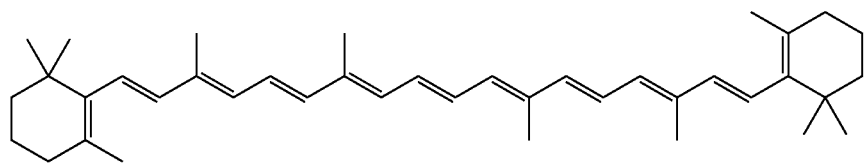

Note that only the all-trans form is shown, but cis isomers may exist as well.

As used herein, "alcohol" includes an organic chemical containing one or more hydroxyl (OH) groups. Alcohols can be liquids, semi-solids or solids at room temperature. Common mono-hydroxyl alcohols include, e.g. methanol, ethanol, isopropyl alcohol, n-propanol, and butanol. Common polyhydroxyl alcohols include, e.g. propylene glycol, ethylene glycol and glycerine. Zeaxanthin in free (non-esterified) form is a diol.

As used herein, "saponifying" or "saponification" includes the process of converting an organic ester into the corresponding alcohol by alkaline hydrolysis. An example of such a hydrolysis is shown:

As used herein, "hydrocarbon" are solvents composed of carbon and hydrogen and are comprised of one or more of the following groups: linear, branched or cyclic alkanes, alkenes, alkynes, and/or aromatic compounds.

As used herein, "washing" includes contacting a substance (optionally dissolved in an organic solvent) with a solvent such as water or methanol or a mixture of solvents, thereby

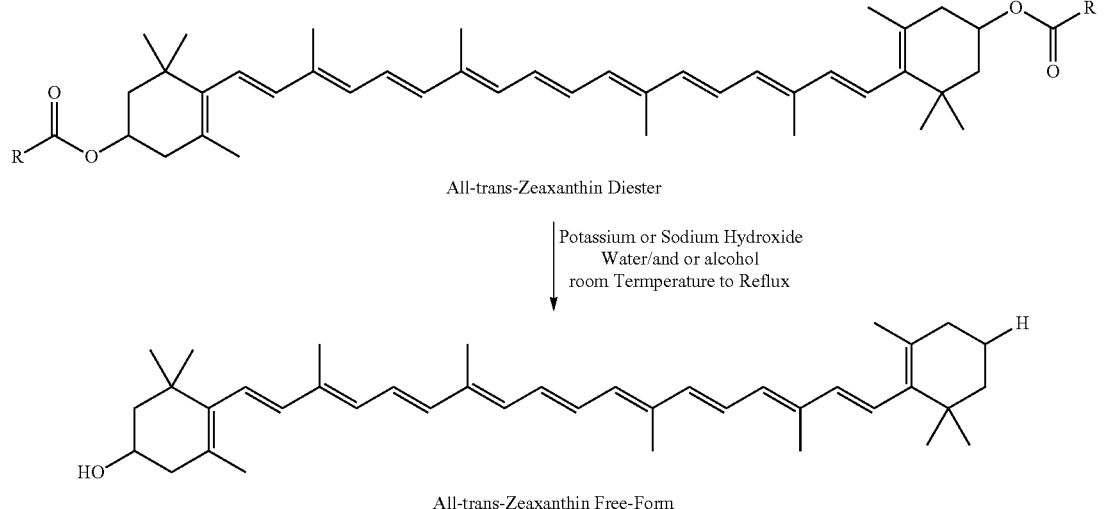

All-trans-Zeaxanthin Diester

Potassium or Sodium Hydroxide
Water/and or alcohol
room Termperature to Reflux

All-trans-Zeaxanthin Free-Form

As used herein "alkali metal" includes any of the monovalent metals of Group I of the periodic able (e.g. lithium, sodium, or potassium). The hydroxides of the alkali metals are strongly alkaline or basic.

As used herein "alkaline earth metal" includes any of the di-valent metals of Group II of the periodic able (e.g. magnesium, calcium or barium). The hydroxides and carbonates of the alkaline earth metals are alkaline or basic.

As used herein, "decanting" or "decantation" includes pouring or pumping off a fluid, leaving a liquid, slurry, sediment, or precipitate, thereby separating the fluid from the other phase.

As used herein, "filtering" or "filtration" includes the passage of a liquid through a filter, accomplished by gravity, pressure or vacuum. The filtering effectively separates the sediment or precipitate from the fluid (filtrate).

As used herein, "centrifuging" or "centrifugation" includes the process or separating fractions of systems in a centrifuge. The most basic separation is to sediment a pellet at the bottom of the tube, leaving a supernatant at a given centrifugal force. In this case sedimentation is determined by size and density of the particles in the system amongst other factors. Density can be used as a basis for sedimentation in density gradient centrifugation at very high g values molecules can be separated, i.e. ultra centrifugation. In continuous centrifugation the supernatant is removed continuously as it is formed. It includes separating molecules or particles by size or density using centrifugal forces generated by a spinning rotor. G-forces of several hundred thousand times gravity are generated in ultracentrifugation. Centrifuging effectively separates the sediment or precipitate from the fluid.

As used herein, "polar solvent" includes solvents that have high dipole moments, wide separation of charges or tight association, e.g. water, alcohols, and acids.

forming at least two phases—including a wash phase and a product phase, optionally mixing and/or shaking, and subsequently separating the phases. The wash phase is a liquid and the product phase may be a solid or a liquid. The removal of the wash phase brings with it soluble impurities. The term includes contacting an organic solid with a wash solvent to remove soluble impurities. It also includes contacting a liquid with an immiscible wash solvent to remove impurities from the liquid.

As used herein, "drying" includes removing a substantial portion of the organic solvent and water present therein.

As used herein "spray drying" includes taking a solution or dispersion and pumping a stream of this dispersion or solution such that it contacts a rotating disk or other dispersal mechanism, typically at elevated temperature and reduced pressure, thereby removing the solvent and forming a fine particulate solid that is collected.

As used herein, "macular degeneration" includes the breakdown or damage to a portion of the retina known as the macula. Symptoms include blurring or distortion of vision (in central vision field), colors appear dim and difficulty reading or performing work up close.

As used herein, "xanthophyll" includes carotenoids that contain at least one oxygen atom, such as zeaxanthin, lutein, capsanthin, capsorubin, astaxanthin, violaxanthin, cryptoxanthin, and antheraxanthin. The hydroxyl-containing carotenoids are often found as esters in the plant material. They usually are found as diesters of fatty acids such as oleic, linoleic, linolenic, and the like.

As used herein, "Carotene" includes those carotenoids which only contain carbon and hydrogen atoms; examples include alpha and beta carotene and lycopene.

As used herein, "Base" includes those materials that are capable of removing a proton from a material, such as an organic acid or an alcohol. Examples of such bases are sodium, potassium, magnesium, calcium, barium hydroxides, and similar metal salts of carbonate, alkoxide or the like.

As used herein, "isohexanes" means a commercial source of hydrocarbons comprising of a mixture of methylpentanes, dimethylbutanes, methylcyclopentane, and not more than 10% n-hexane by weight.

As used herein, "Chinese wolfberries" refers to the fruits of *Lycium barbarum* or *Lycium chinense*.

As used herein, 'marigold flowers' refers to the flowers of *Tagetes erecta*.

As used herein, 'paprika' refers to the fruits of *Capsicum annuum* L.

A method for carrying out the invention is as follows:

a) contacting xanthophyll esters with a hydrocarbon, with an oleoresin:hydrocarbon in the ratio* of 1:0.5 to 1:10, including oleoresin:hydrocarbon 1:1.5, and where the hydrocarbon is hexane or a mixture of low boiling hydrocarbons;
b) addition of an alcohol at an oleoresin to alcohol ratio of 1:1 to 1:10, including oleoresin:alcohol ratio of 1:3, wherein the alcohol is selected from methanol, ethanol and/or any one to four carbon alcohol;
c) addition of base at an oleoresin:base ratio of 10:1 to 1:1, including oleoresin:potassium hydroxide 1:1.2, with the potassium hydroxide added as a 45% aqueous solution, other bases such as the hydroxides, carbonates and alkoxides of alkali and alkaline earth metals can be employed;
b) applying a blanket of an inert gas, selected from, but not limited to nitrogen and argon;
e) applying heat, if necessary, to at least 20° C. up to reflux temperature, including 50-80° C.;
f) allowing the mixture to stir and/or reflux under the inert atmosphere for 0.25 to 120 hrs, including 24 hrs;
g) reducing the temperature of the reaction mixture to 0 to 50° C., preferably to 20-25° C.;
h) allowing the mixture to settle for 0.1 to 1000 hours, preferably 0.5 hours;
i) removing the upper hydrocarbon phase rich in carotenes, including alpha-carotene, beta-carotene, lycopene, and the xanthophyll, beta-cryptoxanthin;
j) optionally adding more hydrocarbon to the remaining reaction mixture with stirring and repeating steps h) and i);
k) desolventizing the upper hydrocarbon phase(s) to obtain a carotene concentrate;
l) adding water, optionally mixed with an alcohol and/or complexing or chelating agent, to the lower phase remaining after hydrocarbon removal with an oleoresin:water ratio* of 1:0.1 to 1:5, including 1:1.5, then thoroughly mixing;
m) allowing the system to settle undisturbed for 0.5 to 1000 hours, including 4 hours;
n) draining the lower aqueous phase (first water wash) rich in soaps and other polar soluble materials;
o) optionally repeating steps l) through n) one or more times;
p) adding an alcohol to the mixture, preferably methanol, optionally adjusting the water content of the mixture to 1-15%, including 2.8%, by alcohol addition and/or concurrent or subsequent distillation;
q) optionally removing the remaining hydrocarbon via distillation;
r) separating the solid precipitated xanthophylls from the liquid supernatant, by decanting, centrifugation, or filtration;
s) adding to the solid xanthophylls a wash solvent and mixing to form a slurry;
t) separating the solid xanthophylls from the wash solvent by decanting or centrifuging;
u) optionally repeating steps s) and t) until the required purity is achieved;
v) removing the solvent(s) and drying;
w) packaging the dried xanthophylls obtained in the preceding step in an inert environment, preferably vacuum packaging or packaging inerted with nitrogen or argon;
x) optionally, precipitating more solid xanthophylls from the liquid supernatant generated in steps r) and t) by addition of water and/or allowing the supernatant to stand for one or more days, and isolating the precipitate thereby formed by filtration, centrifugation, and/or decantation;
y) optionally, repeating step x) until no more precipitate is formed; and
z) optionally desolventizing at step x) to recover the xanthophylls;
aa) optionally adding an antioxidant to the solid prior to desolventizing at steps v), and/or x) and/or z);
ab) optionally extracting the xanthophylls from the precipitate at step v), and/or x) and/or z) with a suitable solvent such as methylene chloride prior to desolventization; and
ac) optionally adding water to the precipitate in step ab) prior to extracting;
ad) optionally raising the temperature of the mixture to 40° C. to 60° C. after draining the water in step n) and isolating the zeaxanthin rich precipitate layer which forms at the bottom of the vessel; and
ae) optionally repeating steps z), aa), ab), and/or ac) with the precipitate layer formed in step ad).

*All ratios unless otherwise specified are weight/weight ratios.

The present invention encompasses not only a product-by-process, but also, the method of forming free-form xanthophylls. Thus, broadly, the instant invention covers a method of treating a plant extract containing at least some esterified xanthophylls, comprising the steps of treating said plant extract in situ with an alcohol, a base capable of saponification, and a hydrocarbon at a temperature between room temperature and reflux temperature of the solvent mixture (less than 200° C.). The resulting saponification mixture is then treated as described above to isolate the free-form xanthophyll product in almost exclusively the all trans form.

The method of the invention uses as a starting material a xanthophyll ester containing material, preferably pods or plant material or extracts from *Capsicum*, in particular, orange paprika. An excellent source of zeaxanthin is the fruit pods of orange paprika *Capsicum annuum* which exhibit in the dried ripe fruit flesh, a hyperaccumulation of carotenoid pigment, wherein zeaxanthin is the dominant carotenoid (Todd, et al., U.S. Application Publication No. US 2006/0185034).

The method of the invention uses an alcohol having one to four carbons. The base used in the method of the invention can be selected from the group consisting of potassium hydroxide, sodium hydroxide, sodium methoxide, sodium ethoxide, potassium methoxide, potassium ethoxide, sodium carbonate, potassium carbonate, and the like. The hydrocarbon used may be selected from any mixture of five, six, seven, and/or eight carbon linear, branched and/or cyclic alkanes, alkenes, alkynes, and/or aromatic hydrocarbons.

Importance of Starting Material

In much of the art cited above, specific examples are given wherein lutein is isolated and/or purified from marigold oleoresin, and based on those results the authors extrapolate their process to be effective also for isolation of the very closely related compound, namely, zeaxanthin, from other sources such as Chinese wolfberry or *Capsicum* oleoresin. It must be stressed that marigold oleoresin of commerce is produced from flower petals and/or a real parts of the marigold plant harvested when the plant is flowering. Chinese wolfberry oleoresin is produced from the fruits of various members of the genus *Lycium*. On the other hand, *Capsicum* oleoresin is produced from the ripe fruits of *Capsicum annuum*. Aside from certain carotenoids and other ubiquitous phytochemicals, the chemical profiles of marigold oleoresin and wolfberry oleoresin are quite different than that of *Capsicum* oleoresin. Because their chemical profiles are so different, it is not surprising that their overall behavior in these complex saponification systems are so different (See Example 10).

Importance of Carotene Recovery

It is common for xanthophyll-ester-containing oleoresins to also contain carotenes with significant potential health benefits, e.g. alpha-carotene, beta-carotene, and lycopene. The process described herein allows for recovery of such carotenes in concentrated form, in addition to and as a separate fraction from the highly concentrated zeaxanthin, thus affording at least two products from a single process.

Effect of Base Amount, Methanol Amount, Temperature from Designed Experiments

As shown in Example 1 the amount of base and alcohol, as well as the temperature at which the reaction is carried out, all have an influence on both the yield of zeaxanthin as well as its purity in the final product. The optimal results in this study were obtained in the presence of hexane and most particularly, the preferable conditions employed 20 mL 45% potassium hydroxide, 40 mL hexane, 70 mL methanol, refluxed for one hour with 20 g of orange paprika oleoresin (see reaction #19 in Example 1). The reaction yields (yields measured by HPLC prior to workup, or HPLC yields, see Example 20) were >99% free zeaxanthin, and resulted in recovery of 117% of the trans-zeaxanthin and 71% of the cis-zeaxanthin that was present in the initial unsaponified oleoresin. This indicates that cis zeaxanthin present in the starting oleoresin was converted to trans zeaxanthin to some extent during the reaction. It should be noted that the sample preparation and analysis conditions for HPLC involve a low-temperature saponification reaction which we have shown (see Example 20) does not cause cis/trans isomerization. After a simple workup procedure, this reaction produced a product providing a 65% isolated yield of zeaxanthin, (92% isolated yield of trans based on the amount of trans present in the starting oleoresin), with 52.1% purity after 2 methanol washes. In order to further optimize yields and purities, it was necessary to investigate other factors, as demonstrated in Example 2.

One object of the present invention is to obtain zeaxanthin in the highest isolated yields and purities, so other processing steps were implemented to meet those important objectives. Conditions were run (Example 2) wherein the hexane was removed from the reaction mixture by distillation prior to workup, providing a product with 81.2% isolated yield of zeaxanthin (113.7% isolated yield of trans) with 17.4% purity prior to washing with methanol. Other conditions gave higher isolated yields with lower purities or higher purities with lower isolated yields. Depending on the needs of the application, one of these examples may be preferable to others depending on purity, cost, and yield requirements. This provides flexibility depending upon the needs of the final product characteristics. The highest total yield of zeaxanthin is obtained using a method outlined in Example 8, wherein 92% of the input zeaxanthin, including 130% of input trans-zeaxanthin, was recovered as a solid in three separate fractions, the highest of which was 38.1% pure. The highest purity of zeaxanthin recovered in the absence of any chromatography was achieved using methylene chloride and is described in Example 11, wherein crystalline all-trans-zeaxanthin was recovered at a purity of 95.1%, but the overall yield for that procedure was only about 13%. The highest purity obtained using only alcohols, hydrocarbons, base, and water was 73.2%, corresponding to a 50% yield (see reaction #14 in Example 1).

Importance of pH

The zeaxanthin derived from orange paprika is quite stable in a basic medium. This is unexpected based on the teaching of the of those skilled in the art [Khachik, et al., (1986); Kimura, et al., (1990); Rodriguez-Bernaldo de Quiros and Costa, (2006); Granado, et al., (1992); Scott, et al., (1992); Hart and Scott, (1995)]. After the saponification in basic media, a pH adjustment or titration step is often taught (see U.S. Pat. Nos. 6,221,417; 6,262,284; U.S. Application Publication No. US 2007/0032683; U.S. Pat. No. 7,173,145). In the processes described herein, there are several different steps in which an acid titration was attempted. When the instant xanthophyll mixture was titrated directly after the reaction was complete, the saponification products of the triacylglycerols present in the oleoresin, i.e. long-chain alkanoates, precipitated, and thereby, introduced an additional challenge to isolating the precipitated zeaxanthin. Large volumes of hexane would be required to dissolve away the precipitated fatty acids (See Example 9) and, as such, would be impractical on an industrial scale.

Importance of Level of Water on Yield

The water content affects the compactability of the solids during the separation step when the methanol supernatant is removed from the solid zeaxanthin. If the water level is too high or too low, the solids do not settle adequately and large amounts of zeaxanthin can be lost during the solid/liquid separation step. An optimum water level for solids compaction is approximately 3%. (See Example 7).

Importance of the Water Washes (Size & Number)

An efficient manner in which to remove the soaps formed during the saponification reaction is to wash the reaction mixture with water. In addition, the size and number of water washes have an effect on both yield and purity of the final product. As shown in Example 4, two water washes resulted in higher yield and higher purity of zeaxanthin in the final product than did one water wash. Unexpectedly, attempts to carry out a third water wash and/or aqueous alcohol wash resulted in a persistent emulsion.

Importance of the Methanol Washes (Size & Number)

In order to achieve target purity levels, it is necessary to further wash the precipitated zeaxanthin with an alcohol such as methanol. As shown in the table in Example 1, the highest purity achieved in the absence of an alcohol wash was about 20%, and typically it was less than 20%. In Example 13 a comparison is given between one and two water washes in conjunction with one and three alcohol (methanol) washes, and also with large (nine times precipitate weight) and small (three times precipitate weight) volumes of methanol. One first observes that isolated yields were higher with two water washes. For two water washes, comparing one large methanol wash with three small methanol washes, i.e. the same amount of total alcohol was used, the overall yield of zeaxanthin was similar, however the purity of the zeaxanthin obtained was 21.5% (wt %) in the case of one large wash, and 66.1% in the case of three small washes. Three large methanol washes provided similar, but slightly larger purity (70.3%), but a reduced yield (39% vs. 48%). The best overall results were obtained with two water washes and three small methanol washes. The smaller methanol washes allow for larger amounts of input oleoresin into the reactor and therefore greater throughput.

Importance of Adding Hexane-beta Carotene Isolation, Reaction Rate, Purity of Zeaxanthin Addition of hexane is advantageous in three specific stages in the process described herein; the reaction itself, recovery of carotenes, and removal of soaps.

Advantage one. When added to the reaction mixture, hexane helps to dissolve the oleoresin and increases contact between zeaxanthin esters and base, thereby accelerating the reaction rate. Compare the kinetic data in Example 1. Reaction #2 in Example 1 was done in 24 hrs using 40 ml methanol and 30 ml of 45% potassium hydroxide at room temp, whereas reaction #18 was done in only 3.5 hr using less base (20 ml) by adding 40 ml hexane at the beginning of the reaction. All the other factors were identical except that less base was used in reaction #18 and this should have slowed the reaction.

Advantage two. After the reaction is complete and the mixture was allowed to settle, the added hexane unexpectedly created a three-liquid-phase solvent system wherein the uppermost phase was nearly 100% hexane, containing a majority of the carotenes present in the oleoresin, thereby allowing facile recovery of the high-value carotenes with a decant procedure. The carotenes from *Capsicum* were typically recovered as about a 10% carotene material, the carotene content of which was predominantly β-carotene (>80%), and also contained the valuable carotenoids α-carotene and β-cryptoxanthin. This had the added effect of contributing to a higher purity zeaxanthin product.

Advantage three. After decanting the upper carotene phase, the hexane in the remaining two-liquid-phase system allowed for facile removal of considerable quantities of soaps by partitioning with water; without hexane only a one-phase system was created thereby significantly complicating the process of soap removal.

Importance of Hexane Removal—Yield

It has been shown that yields of zeaxanthin in the isolated precipitate are increased considerably if the hexane is removed prior to isolation of the precipitate (See Example 2). After washing away the soaps with water, a highly viscous, jellylike, gummy mixture is formed that does not settle into layers even after several days. When methanol is added, the gummy mixture settles instantly into a two liquid phase system along with precipitated zeaxanthin. About 35% of the total zeaxanthin is dissolved in the upper hexane/methanol phase of the binary system. When this two-liquid-phase system is distilled until all hexane is removed, less than 20% of the total zeaxanthin remains dissolved in solution. Removal of the hexane therefore increases zeaxanthin yield in the recovered precipitate by at least 15%. This dependency of yield on hexane level in an alcohol/alkane/water reaction system has not previously been described in the art.

Problems Inherent in the Addition of Calcium Acetate on Purity, Yield, Ease of Handling The addition of calcium acetate and/or other complexing agents is often taught as an efficient procedure for removal of alkanoates after a saponification reaction. In the process described herein, the zeaxanthin is highly insoluble and is isolated as a solid precipitate. Attempts to add complexing agents to precipitate soaps therefore only further complicated the process of isolating solid zeaxanthin. Calcium acetate actually formed a persistent emulsion that made isolation of zeaxanthin very difficult (See Example 26).

Solubility of Zeaxanthin vs. Lutein

The solubilities of zeaxanthin and its isomer, lutein, have been compared (see Example 11). There is considerable prior art describing the saponification of lutein esters. Simply applying lutein process conditions to zeaxanthin, which appears reasonable at first blush, is problematic due to the differences in solubility of these two materials. It is therefore not helpful that the prior art related to industrial scale production of generic xanthophylls teaches steps that would require the dissolution of zeaxanthin in a solvent, when this compound has limited solubility in many apolar and protic solvents (see Example 11). Such a process would require inordinate volumes of any solvent other than tetrahydrofuran or dichloromethane, or would be a less efficient extraction process with, among others, the other solvents listed in Example 11.

For instance, U.S. Pat. No. 5,602,286 teaches the use of alcohol, preferably ethanol, refluxing xanthophylls from corn gluten with potassium hydroxide, filtering the solution and evaporating the filtrate to obtain refined xanthophylls. The crude corn gluten was extracted with ethanol to provide 5 grams of crude xanthophylls, which contained about 12.7 mg of xanthophylls. This was refluxed in 5 mL of ethanolic potassium hydroxide and then washed with 50 mL of ethanol. The filtrate was collected and evaporated to recover about 18.5 mg xanthophylls. For these 18.5 mg to be soluble, would require a solubility of about 18.5 mg/0.055 L=336.5 mg/L of xanthophyll. While this is very similar to the reported literature solubility of lutein (300 mg/L ethanol), it is very far away from the measured solubility of zeaxanthin from this work (40 mg/L of ethanol). It seems very unlikely that these conditions could be used on an industrial scale to isolate zeaxanthin.

Reaction Time vs. % Trans Recovery

As previously discussed (Englert, et al., 1991; Isler, et al. 1956; Karrer and Jucker, 1950; U.S. Pat. Nos. 2,849,507; 3,441,623; Zechmeister 1962; Surmatis, U.S. Pat. No. 3,989,757), the cis-isomers of zeaxanthin can be converted to the relatively insoluble trans-isomer by refluxing an alcohol solution. As shown in Example 1 with factors other than reaction time being equal, both the reaction yields and purities of the trans zeaxanthin increased with reaction time. This phenomenon was reflected in the trans/total zeaxanthin recovered in the solid (>95% for reactions 14-26; see Table 3 in Example 1) compared with that recovered in the soluble side legs (as low as 22%). The isolated yields showed the trend of increasing for at least the first 24 hours as evidenced by reactions 19-22, wherein the isolated zeaxanthin yield increased from 51% to 65% and at the same time the purity increased from 40.1% to 52.1% as the mixture is refluxed from 1 to 24 hrs. While this seems consistent with the teaching of the art referenced above, it is the opposite of what is expected according to the teaching of the art for the fact that an alcohol and strong base was used. According to the teaching of the cited references with regard to results under similar conditions, using alcohol and strong base at pH 14, we should have observed decomposition under these strongly basic conditions. Furthermore, the data in Example 3 also show that at reflux in very basic aqueous methanolic solution, the % trans zeaxanthin also increased over time as the % cis zeaxanthin decreases, all while the % total zeaxanthin remained relatively constant. This indicates that zeaxanthin is stable to degradation under these conditions, but that the cis isomer converted to the more desirable trans isomer, which also resulted in an increased isolated yield.

Partitioning into Dichloromethane and Other Solvents

It was possible to partition zeaxanthin from the final methanol-washed slurry into another solvent better suited for subsequent operations such as making beadlets via spray drying. Examples of other solvents include dichloromethane, a good solvent for zeaxanthin. Example 5 shows that zeaxanthin can be successfully partitioned into dichloromethane via continuous extraction from the point in the reaction where the hexane is decanted. Water and dichloromethane were added and a 99.7% yield of zeaxanthin from the starting oleoresin was recovered having a purity of 20.6%. Subsequent water washing improved the purity. Example 11 shows the results of performing the water washes and methanol washes in our optimal procedure prior to doing the extraction into dichloromethane. The result was the isolation of 95% pure all-trans-zeaxanthin, with no other detectable carotenoids. Dichloromethane is a good solvent for these partitionings. It is second only to tetrahydrofuran (in this study) in its ability to solubilize zeaxanthin. However, this technique should not be limited to dichloromethane. Any solvent which can solubilize zeaxanthin such as ethyl acetate, methyl tert-butyl ether or the like can be used. Preferably the solvent should be immiscible with methanol under the conditions used to allow for more efficient extraction of the zeaxanthin without other impurities being extracted as well. Anyone skilled in the art can combine the water and methanol washes in different ways to optimize the yield and purity of zeaxanthin from dichloromethane partitioning and/or extraction from the methanol slurry resulting from saponification. Furthermore, anyone skilled in the art could optimize other extraction solvents used in place of dichloromethane.

Importance of Temperature in Zeaxanthin Yield and Purity

Temperature control during workup of the orange paprika zeaxanthin saponification has been shown to be a factor for obtaining high yields and purity (Example 8). Saponification was performed and followed by a single water wash, after which the vessel was brought to 60° C. without any stirring. A compacted layer of solids formed on the bottom of the vessel. This layer was isolated, homogenized with methanol, centrifuged, and decanted to afford a refined precipitate that, after desolventization, contained zeaxanthin at 59.4% purity corresponding to a 67% yield. One skilled in the art could optimize the size and number of water washes coupled with temperature control to maximize both yield and purity.

Importance of Different Alcohols vs. Water on Purity & Yield

From an economic perspective, it would be most advantageous to carry out a saponification process entirely in water. It is possible to carry the saponification reaction to completion in an aqueous medium, however the soaps thereby created and their interactions with water create a system that does not readily allow isolation of zeaxanthin in sufficient purity and/or yield for the purposes described herein. The use of various alcohols as co-solvents was investigated, and the use of ethanol and methanol both provided material with sufficient purity, particularly when an alkane was added as described herein. Methanol is the best commercial choice of alcohol for cost concerns. For cases where residual solvent is a concern, and cost is less of an issue, food-grade ethanol may prove the solvent of choice.

The process of the present invention starts with oleoresin that has not been subjected to the pre-extraction procedures. In the instant process the starting material is derived from *Capsicum*, those skilled in the art understand that the types and amounts of xanthophylls which may be effectively isolated are dependent on the source of plant material. Further, the instant process is suitable for saponifying oleoresins that contain relatively low levels of xanthophyll esters, as well as higher levels. Many processes of the cited art do not contain sufficient purification steps to achieve high levels of purity from oleoresins with xanthophylls in the 1-3% range. At these levels, the interferences from the high concentrations of soaps (from the saponified vegetable oils) makes isolation problematic, while at the same time there is a high enough concentration of xanthophyll, such that a portion of it is insoluble enough to make extraction and complete dissolution of the xanthophylls a costly, time-consuming operation.

Second, the zeaxanthin yields (up to 80%) and purity (up to 70%) obtained using the instant process are very sensitive to the workup conditions, and it is these workup processes that are the subject of this disclosure.

The HPLC methods to separate, identify and quantify carotenoids such as beta-cryptoxanthin, alpha-carotene and beta-carotene, capsanthin, capsorubin and other carotenoids are described in Todd, et al (U.S. Application Publication No. US 2006/0185034). Zeaxanthin was quantified as outlined in Example 20.

All patents and publications cited in this application are herein incorporated by reference.

EXPERIMENTAL PART

The present invention will be better understood in connection with the following examples, which are intended as an illustration of and not a limitation upon the scope of the invention. It will be apparent to those skilled in the art that the described examples are merely representative in nature.

Example 1

A series of reactions were carried out in order to investigate the effect of base type (hydroxide vs. methoxide), base amount, methanol amount, presence or absence of an alkane (hexane), and temperature (room temperature or reflux). Each reaction was carried out as follows: To a three-neck reaction flask was added 20 g of paprika oleoresin containing 2.7% total zeaxanthin comprised of 1.9% trans-zeaxanthin and 0.8% cis-zeaxanthin (mixture of isomers), along with the other reagents and proportions shown in the table below. Hexanes and methanol were both HPLC grade from Fisher scientific. When potassium hydroxide was used as the base, it was added as a 45% aqueous solution. When sodium methoxide (NaOMe) was used, it was added as a 30% solution in methanol. After the reagents were added, positive nitrogen pressure was promptly applied to the flask, and the reactants continuously mixed with an overhead stirrer for the duration of the reaction. With the exception of reactions 9 and 10, all reactions were carried out either at room temperature or at reflux. The reactions were monitored by HPLC and allowed to proceed until it was determined that the reaction was >95% complete, or until 24 hrs had passed, whichever occurred first. When the reaction was stopped, the mixture was transferred to a tared centrifuge bottle, centrifuged, and then decanted to afford a supernatant and a crude precipitate. Except for reactions 24-27, the crude precipitate was washed twice with methanol. The amount of methanol added was four times by mass of the crude precipitate. For each wash step, methanol was added and the mixture was shaken vigorously, then centrifuged and decanted to afford a wash solution and a refined precipitate. The zeaxanthin content in the refined precipitates is shown in Table 3. The total zeaxanthin recovery is given in the last three columns of Table 3, and it is noted that essentially all of the cis-zeaxanthin recovered was soluble in either the supernatant or wash solutions. The total zeaxanthin recovery column in Table 3 shows the mass balance of total, cis and trans zeaxanthin for isolated precipitate was well as the wash and supernatant legs.

TABLE 3

Summary of experiments designed to optimize type of base, amount of base, amount of methanol, and effect of alkane addition.

| | reaction conditions | | | | | | | | isolated precipitate | | | | | | saponified zeaxanthin recovery (precipitate + side legs) | | |
|---|---|---|---|---|---|---|---|---|---|---|---|---|---|---|---|---|---|
| reaction # | reaction hexane (ml) | reaction MeOH (ml) | Base type | base volume (ml) | reaction temp (°C) | time to >95% reaction yield (hr) | Total reaction time (h) | Total MeOH wash (ml) | precipitate dry mass (g) | purity (total ZX wt %) | cis-ZX wt % | YIELD (total ZX output/input) | YIELD (trans-ZX) | YIELD (cis-ZX) | total ZX recovered (% of input) | trans-ZX recovered (% of input) | cis-ZX recovered (% of input) |
| 1 | 0 | 40 | KOH | 15 | 22 | >24 | 24 | 156 | 0.7669 | 31.7 | 0.4 | 45% | 63% | 2% | 88% | 92% | 49% |
| 2 | 0 | 40 | KOH | 30 | 22 | 24 | 24 | 250 | 0.9574 | 27.9 | 0.4 | 49% | 69% | 2% | 92% | 96% | 46% |
| 3 | 0 | 40 | KOH | 15 | 77 | 3 | 4.25 | 139 | 1.5580 | 22.5 | 0.3 | 65% | 91% | 3% | 97% | 107% | 58% |
| 4 | 0 | 100 | KOH | 15 | 72 | 1.25 | 5 | 223 | 1.6080 | 21.2 | 0.2 | 63% | 88% | 2% | 101% | 114% | 37% |
| 5 | 0 | 100 | KOH | 15 | 77 | 4 | 4.25 | 256 | 1.8100 | 18.4 | 0.2 | 62% | 86% | 3% | 101% | 108% | 62% |
| 6 | 0 | 40 | KOH | 15 | 22 | >24 | 24 | 152 | 0.8746 | 15.3 | 0.3 | 25% | 34% | 1% | 61% | 55% | 54% |
| 7 | 0 | 100 | KOH | 15 | 77 | 1 | 5.25 | 182 | 1.7430 | 13.8 | 0.3 | 44% | 62% | 3% | 108% | 117% | 51% |
| 8 | 0 | 100 | KOH | 30 | 78 | 1 | 5 | 349 | 2.5479 | 12.6 | 0.2 | 59% | 83% | 4% | 98% | 109% | 23% |
| 9 | 0 | 70 | KOH | 22.5 | 47.5 | 4 | 4.25 | 258 | 2.9450 | 12.5 | 0.1 | 68% | 96% | 2% | 112% | 121% | 54% |
| 10 | 0 | 70 | KOH | 22.5 | 47.5 | 4 | 4.25 | 338 | 2.7290 | 11.2 | 0.3 | 56% | 78% | 4% | 95% | 97% | 47% |
| 11 | 0 | 100 | KOH | 30 | 22 | >24 | 24 | 208 | 1.3642 | 8.0 | 0.1 | 20% | 28% | 1% | 57% | 52% | 43% |
| 12 | 0 | 40 | KOH | 30 | 83 | 2.5 | 4.25 | 278 | 4.5200 | 6.8 | 0.2 | 57% | 78% | 6% | 96% | 100% | 37% |
| 13 | 0 | 40 | KOH | 30 | 83 | 2 | 5.25 | 320 | 3.5050 | 3.3 | 0.1 | 22% | 29% | 3% | 97% | 92% | 40% |
| 14 | 0 | 40 | KOH | 5 | 22 | >24 | 24 | 40 | 0.3676 | 73.2 | 0.2 | 50% | 71% | 0% | 79% | 91% | 39% |
| 15 | 40 | 40 | KOH | 5 | 52 | 6 | 24 | 40 | 0.4138 | 68.7 | 0.2 | 53% | 75% | 0% | 80% | 92% | 41% |
| 16 | 40 | 40 | KOH | 20 | 55 | 0.25 | 5 | 67 | 0.4867 | 68.3 | 0.2 | 61% | 87% | 0% | 96% | 105% | 18% |
| 17 | 40 | 40 | KOH | 20 | 22 | 2.5 | 5 | 44 | 0.5819 | 60.6 | 0.5 | 65% | 91% | 2% | 104% | 119% | 66% |
| 18 | 40 | 40 | KOH | 20 | 22 | 3.5 | 5 | 97 | 0.3611 | 56.0 | 0.0 | 37% | 53% | 0% | 99% | 100% | 81% |
| 19 | 40 | 70 | KOH | 20 | 52 | 1 | 24 | 44 | 0.6960 | 52.1 | 0.0 | 65% | 92% | 0% | 103% | 117% | 71% |
| 20 | 40 | 70 | KOH | 20 | 52 | 1 | 8 | 45 | 0.6644 | 44.2 | 0.0 | 55% | 77% | 0% | 101% | 109% | 79% |
| 21 | 40 | 70 | KOH | 20 | 52 | 1 | 4 | 60 | 0.6537 | 42.6 | 0.0 | 52% | 73% | 0% | 98% | 106% | 80% |
| 22 | 40 | 70 | KOH | 20 | 52 | 1 | 1 | 65 | 0.6889 | 40.1 | 0.0 | 51% | 72% | 0% | 94% | 103% | 72% |
| 23 | 40 | 100 | KOH | 5 | 22 | >24 | 24 | 45 | 0.5915 | 29.8 | 0.1 | 33% | 46% | 0% | 89% | 96% | 67% |
| 24 | 40 | 100 | KOH | 5 | 22 | 24 | 30 | 0 | 1.2435 | 20.1 | 0.2 | 45% | 64% | 2% | 92% | 93% | 89% |
| 25 | 40 | 40 | KOH | 20 | 22 | 24 | 4 | 0 | 2.5581 | 12.8 | 0.2 | 62% | 86% | 3% | 105% | 113% | 87% |
| 26 | 40 | 40 | KOH | 20 | 22 | 1 | 6 | 0 | 2.7272 | 12.5 | 0.2 | 63% | 88% | 3% | 102% | 114% | 76% |
| 27 | 40 | 40 | KOH | 5 | 52 | 2.5 | 6 | 0 | 3.7227 | 9.2 | 0.4 | 65% | 88% | 9% | 97% | 103% | 84% |
| 28 | 0 | 100 | NaOMe | 40 | 72 | 2 | 6 | 200 | 0.6800 | 45.8 | 0.0 | 58% | 82% | 0% | 106% | 106% | 85% |
| 29 | 0 | 40 | NaOMe | 5 | 72 | 5 | 6 | 120 | 0.6974 | 44.2 | 0.0 | 57% | 81% | 0% | 106% | 117% | 71% |
| 30 | 0 | 40 | NaOMe | 5 | 72 | 2 | 2 | 105 | 0.5500 | 43.7 | 0.3 | 45% | 63% | 1% | 103% | 103% | 92% |
| 31 | 0 | 100 | NaOMe | 40 | 72 | 2 | 2 | 120 | 0.6683 | 40.4 | 0.0 | 50% | 71% | 0% | 98% | 101% | 76% |
| 32 | 0 | 70 | NaOMe | 22.5 | 22 | 6 | 6 | 76.4 | 0.8208 | 36.7 | 0.3 | 55% | 77% | 2% | 93% | 103% | 60% |
| 33 | 0 | 40 | NaOMe | 40 | 22 | 6 | 7 | 120 | 0.9722 | 34.4 | 0.3 | 62% | 87% | 2% | 94% | 107% | 51% |
| 34 | 0 | 40 | NaOMe | 40 | 22 | 4 | 6 | 120 | 0.7563 | 33.4 | 0.0 | 47% | 66% | 0% | 100% | 103% | 79% |
| 35 | 0 | 100 | NaOMe | 40 | 22 | 4 | 6 | 130 | 0.8257 | 33.1 | 0.3 | 51% | 71% | 1% | 101% | 106% | 75% |
| 36 | 0 | 40 | NaOMe | 40 | 22 | 4 | 6.5 | 120 | 0.7606 | 32.9 | 0.0 | 46% | 66% | 0% | 91% | 96% | 64% |
| 37 | 0 | 40 | NaOMe | 40 | 22 | 4 | 5 | 120 | 0.7710 | 31.5 | 0.0 | 45% | 64% | 0% | 85% | 89% | 59% |
| 38 | 0 | 40 | NaOMe | 40 | 75 | 2 | 6 | 135 | 0.7346 | 30.5 | 0.2 | 42% | 59% | 0% | 94% | 87% | 91% |
| 39 | 0 | 40 | NaOMe | 5 | 22 | >24 | 24 | 61.4 | 0.7021 | 20.3 | 0.2 | 26% | 37% | 1% | 77% | 83% | 54% |
| 40 | 0 | 100 | NaOMe | 5 | 22 | >24 | 24 | 70 | 1.0487 | 2.4 | 0.0 | 5% | 7% | 0% | 50% | 45% | 55% |

For reactions 19-22, the upper hexane layer was decanted from the supernatant, desolventized and analyzed both for zeaxanthin content and for color value. The color value, in standard international color units (SIU), obtained from the hexane phase of reactions 19-22 was 238,590, 228,030, 281,160, and 351,120, respectively, while the zeaxanthin content in all cases was less than 0.1%. Therefore, the hexane layer thereby obtained contained carotenes in highly enriched form. It is noteworthy that in every case the zeaxanthin in the isolated precipitate was almost entirely present in the all-trans form. It should also be noted that, when summing all the outputs, it was quite clear that a portion of the input cis-zeaxanthin was converted to the all-trans isomer during the process. Additionally, we started with oleoresin having 30% of the input zeaxanthin in the cis form. The cis isomer did not precipitate from solution as did the trans isomer. As such total isolated yields were expected to be lower than those starting with an all-trans material. The fact that we recovered greater than 100% of the trans isomer under some of our conditions speaks well for the efficiency as measured by the isolated yields in this process. We were limited, in part, by our ability to achieve complete conversion of the cis to the trans isomer during the reaction. As is seen in Example 8, higher recovered yields of zeaxanthin were achieved from this starting oleoresin by allowing the supernatant to re-equilibrate, so that more trans isomer precipitated out of solution.

Reactions 24 through 27 in Example 1 give representative yields and purities that were obtained by running a procedure similar to that described by Zelkha, et al. on *Capsicum* oleoresin. Yields ranged from 45% to 65% with purities ranging from 9.2% to 20.1%. It should be noted that the 20.1% purity material was obtained in only 45% yield.

Example 2

A reaction was carried out using the same reactants at the same proportions under the same conditions as reaction 19 in the table in Example 1. The procedure was identical for the first 24 hrs as described for reaction 19, but after refluxing for 24 hours, the mixture was allowed to settle for 1 hour at which time the upper hexane layer was decanted away. The remaining lower phase was washed twice by partitioning with water (30 mL for each wash). In each case the lower aqueous phase was discarded and after the second water wash, methanol (75 mL) was added to the remaining upper phase. The mixture was then distilled to remove the remaining hexanes and then refluxed for five hours. The mixture was then allowed to cool and was centrifuged and decanted to afford a supernatant and a crude precipitate. The crude precipitate was desolventized and HPLC analysis showed that 81.2% of the total zeaxanthin input was isolated in the precipitate, including 113.7% of the input all-trans-zeaxanthin. The purity was 17.4%. In a separate experiment, the mixture was allowed to cool after distilling away hexane (i.e. the five hour reflux described above was not carried out) and placed in a separating funnel for 15 days at which time the supernatant was removed by decanting to afford a crude precipitate. It should be noted that no degradation of zeaxanthin was observed after sitting 15 days in this strongly basic solution (pH~14). The crude precipitate was mixed with methanol (ca. 3x by weight of crude precipitate), shaken vigorously, and allowed to settle overnight, then decanted. This methanol wash/decant procedure was repeated one more time to afford a refined precipitate that, after drying, was 42.1% pure zeaxanthin at a 78.5% isolated yield. The supernatant and both wash solutions were analyzed for zeaxanthin content and >99% of the input zeaxanthin was accounted for, even after sitting in caustic solution for two weeks!

Example 3

A demonstration that, among other things, some cis zeaxanthin is converted to trans during the saponification, and that additional cis-zeaxanthin can be converted to trans by incorporating an additional reflux step.

In a procedure similar to that described in Example 2 after distilling away the hexane, the mixture was refluxed for a total of 40 hours and the content of zeaxanthin isomers was monitored by HPLC as a function of time. The results are given in the table below. After refluxing for 40 hours the mixture was allowed to cool, then centrifuged to afford a supernatant and a crude precipitate. The crude precipitate was washed with methanol (4x by weight of crude precipitate) centrifuged and decanted to afford a wash solution and a refined precipitate. After desolventization, the powder was 59.0% pure zeaxanthin corresponding to a yield of 71%. The supernatant and the wash solution were both analyzed for zeaxanthin content and >99% of input zeaxanthin was accounted for, even after refluxing in caustic solution for 40 hours!

TABLE 4

| | Zeaxanthin Content. | |
|---|---|---|
| reflux time | Zeaxanthin HPLC yield (% of input) | |
| (hr) | % trans | % cis |
| 0 | 114.5 | 65.5 |
| 2 | 115.6 | 63.0 |
| 16 | 120.6 | 51.0 |
| 23 | 120.8 | 50.5 |
| 40 | 121.9 | 47.8 |

There was no significant loss in xanthophylls using 45% potassium hydroxide under reflux for up to 40 hr (see Example 3) nor was any significant loss of zeaxanthin observed after allowing the mixture to sit in strongly basic (pH~14) solution at room temperature for 15 days (Example 2). In fact, an increase of the more highly-desired trans isomer via isomerization of the cis isomer of zeaxanthin occurs under these conditions.

Example 4

In an experiment similar to that described in Example 2 a side-by-side experiment was done to determine the effects skipping the second water wash on the final isolated product. Results are as follows:

| | Purity | Total Yield |
|---|---|---|
| 1 water wash | 45.75% | 79.73% |
| 2 water wash | 56.67% | 82.66% |

Example 5

In an experiment with the same reagents and proportions, and conditions as reaction #19 in the table in Example 1, a continuous extraction with dichloromethane was used as an alternative to centrifugation as a means to isolate zeaxanthin from the caustic, soapy reaction mixture. After removing the hexane layer, as described for reactions 19-22 in Example 1, the reaction mixture was placed in a continuous extractor along with two parts water (by mass) and three parts dichloromethane. The dichloromethane was refluxed/percolated through the extractor for a total of 14 hours after which the dichloromethane extract was analyzed for content of zeaxanthin. The dichloromethane extract contained a quantitative yield (99.7%) of the input zeaxanthin, at a purity of 11.9%. Further refining of such a dichloromethane extract by back-extraction with water resulted in an enhanced purity of 20.6%. It is likely that a less exhaustive dichloromethane extraction would have resulted in acceptable recovery of zeaxanthin at higher purity.

Example 6

To a 400 gallon vessel was added 350 lb. Paprika oleoresin containing 2.7% total zeaxanthin comprised of 1.9% trans-zeaxanthin and 0.8% cis-zeaxanthin (mixture of isomers) by weight, 93 gallons isohexanes, 159 gallons methanol, and 43 gallons potassium hydroxide (45% aq.). A nitrogen blanket was applied and the mixture was refluxed at 52° C. for 24 hours at which time it was cooled to 20° C. and the upper hexane layer was decanted from the vessel. At that point 63 gallons of water (prepared by reverse osmosis) were added the vessel, the contents mixed and then allowed to settle for 2 hours at which time the lower aqueous phase was drained from the vessel. An additional 63 gallons of water were added to the vessel, the contents mixed and allowed to settle for 18 hours at which time the lower aqueous phase was drained from the vessel, after which 159 gallons of methanol were added to the vessel, heat was applied and distillate was collected until the boiling point reached 70° C. This effectively removed the remainder of the input isohexanes. The mixture was then refluxed for five hours and allowed to cool. At that point there existed a dark red nearly opaque supernatant with a deep orange precipitate at the bottom. The supernatant was decanted to afford a crude precipitate layer. With the crude precipitate was mixed 73 gallons of methanol to form a slurry that was allowed to settle for 72 hours at which time the supernatant was decanted away to afford a semi-refined precipitate. The precipitate was further refined with second wash using 310 gallons of methanol which, after decanting, afforded 440 pounds of a slurry of zeaxanthin in methanol. This slurry contained 2.6% total solids. A portion of this slurry was desolventized and analysis revealed that the solids contained 55.6% zeaxanthin corresponding to a 67% isolated yield. Approximately 5.2% carotenes, 5.8% beta-cryptoxanthin and 2% capsanthin were found in the solid as well. Centrifugation and filtration are other separation techniques that might prove useful in isolation of zeaxanthin from these reactions.

Workup of initially decanted hexane layer. The hexane was removed from the decanted layer by distillation at reduced pressure to afford 7.9 pounds of a solid paste consisting of 16.7% total carotenoids (See example 19), of which 3.8% was alpha-carotene, 81.8% was beta-carotene, and 7.1% was β-cryptoxanthin, as determined by their relative HPLC area % measured at 450 nm.

Example 7

Demonstrating the effect of continuous distillation with methanol addition and the effect of water content on solids compaction. In a procedure identical to that described in Example 6, after distilling then refluxing for five hours, rather than decant the supernatant immediately, methanol was continuously added as the mixture was distilled. The water content of the mixture was monitored by Karl Fisher titration throughout this process and was found to have a profound effect on the settling time and compaction of the precipitated zeaxanthin, as shown in the table below, which is a key parameter in the subsequent solid/liquid separation step. The faster the settling time, and the better the material compacts, the easier it is to centrifuge and/or decant. When the water content was decreased to 2.8%, the solids settled quite rapidly as compared to the native supernatant; it settled faster and formed a more compact layer under unit gravity. However, when the water content was reduced further to 1.5%, the both the settling time and degree of compaction were worse than in the native supernatant.

TABLE 5

Water Content.

| settling time (min) | water content (wt %) | | |
|---|---|---|---|
| | 11.4% | 2.8% | 1.5% |
| | solids compaction (relative height of clarified supernatant in vessel) | | |
| 0 | 0% | 0% | 0% |
| 30 | 40% | 76% | 26% |
| 60 | 60% | 79% | 42% |
| 120 | 65% | 82% | 45% |
| 240 | 65% | 82% | 45% |

Example 8

Demonstrating the effect of temperature on partitioning. The following experiment is identical to that described in Example 6 up through draining off the first water wash. After removing the first water wash the vessel was brought to 60° C. without any stirring. A compacted layer of solids formed on the bottom of the vessel. This layer was isolated, homogenized with methanol, centrifuged, and decanted to afford a refined precipitate that, after desolventization, contained zeaxanthin at 59.4% purity corresponding to a 67% yield.

In another experiment, the precipitate layer obtained by heating the vessel as above, was dried without further refining to afford zeaxanthin at 38.1% purity and 59% yield. The remaining supernatant was set aside for three days to allow more trans-zeaxanthin to precipitate out. The mixture was then centrifuged to afford a second-pass precipitate and a second-pass supernatant. After drying, the second pass precipitate contained 23.8% zeaxanthin corresponding to a 26.2% yield. The second-pass supernatant was then set aside again for a total of 11 days to allow more precipitation of trans-zeaxanthin and recovery by centrifugation to afford a third-pass precipitate along with a third-pass supernatant. The third-pass precipitate contained 8.6% zeaxanthin by weight corresponding to an additional 4.5% total yield of zeaxanthin in isolated solid form. In summing the initial, second-pass, and third-pass precipitates, 92% of the total zeaxanthin input was recovered in solid form, with enhanced zeaxanthin purity in each fraction compared to the input oleoresin.

Example 9

Demonstrating the effect of ph on process workup.

In a procedure identical to that described in Example 6, after distilling then refluxing for five hours, rather than decant the supernatant immediately, the mixture was titrated with sulfuric acid (30% aq.) to a pH of 5.3. It should be noted that considerably more precipitate was present in titrated solutions than in the native alkaline mixture. The considerably clarified supernatant, obtained at pH of 5.3, was decanted and analyzed. It was found to be completely devoid of zeaxanthin. The solids remaining were homogenized with methanol and allowed to settle overnight at which time the methanol solution was decanted and analyzed to reveal that 9.7% of the input zeaxanthin was dissolved in the methanol solution. The remaining precipitate was again homogenized with methanol, allowed to settle overnight, and decanted to afford a refined precipitate and a second methanol wash solution. The second wash solution contained 2.5% of the input zeaxanthin. After desolventization, the refined solids contained zeaxanthin at 6.2% purity corresponding to a 55% yield of input zeaxanthin. In Example 6, essentially this same workup was carried out, but without titrating (decant supernatant, followed by two methanol washes), and the purity obtained was nearly 10-fold higher (55.6% vs. 6.2%). These numbers reflect the purity lowering effect of acid titration. Therefore, incorporation of an acid titration in the process would necessitate significantly more solvent and a more complicated workup procedure. In an identical experiment, samples of the mixture were sub-sampled at various pH points in order to measure settling time and compaction of the solids. As shown in Table 6 below, the best solids compaction was observed for the native solution (pH=14; 80% compaction) and the worst was a neutral pH. At pH 7.06, solids settled to about 85% of the solution height and did not settle any further, even after more than 7 days. All solutions settled for the same amount of time.

TABLE 6

Settling of precipitates under unit gravity as a function of pH.

| settling time (hr) | pH | | | | | | |
|---|---|---|---|---|---|---|---|
| | 14 | 13.78 | 9.01 | 7.92 | 7.06 | 6.76 | 5.79 |
| | solids compaction (relative height of clarified supernatant in vessel) | | | | | | |
| 12 | 80% | 78% | 69% | 23% | 15% | 39% | 64% |

Example 10

The process described by Montoya-Olvera, et al. was attempted on Todd et al. oleoresin.

It should be noted that marigold oleoresin is the only xanthophyll starting material used in the examples presented by Montoya-Olvera, et al. To a centrifuge bottle were added 40 g of *Capsicum* oleoresin containing 2.7% zeaxanthin. The bottle was placed in a water bath at 40° C. and gently agitated for 15 minutes at which time 40 g of a solution of $Na_2CO_3$ (2.5% aq.) was added. The mixture was agitated at 40° C. for 30 minutes, then centrifuged at 2700×g for one hour. No layer separation was observed after centrifuging for one hour. After two hours, a slight upper organic layer began to appear. After six hours of centrifuging a lower phase began to appear, and the size of upper layer had increased slightly more, but over 95% of the total volume was still a persistent emulsion. At this point it was decided that this process is not practical when using Todd et al. *Capsicum* oleoresin as an input.

Example 11

Demonstrating continuous extraction with dichloromethane to make highly pure zeaxanthin and solubility results.

In a procedure identical to that described in Example 6 up until almost the final methanol desolventization step, rather than desolventizing the zeaxanthin methanol slurry, it was transferred along with 1.5 parts water (by volume) to a continuous extractor containing 1 part dichloromethane. The slurry was extracted with dichloromethane for four hours at which time the dichloromethane solution in the receiver was decanted away from the crystalline zeaxanthin that had formed. The crystals thereby obtained were 95.1% pure all-trans-zeaxanthin. The yield obtained was only 12.6%, but this experiment was only intended to produce purified zeaxanthin crystals. Anyone skilled in the art could certainly optimize this procedure to achieve a significantly higher yield. These crystals were homogenized in a mortar and pestle and added to separate vials containing various solvents until a saturated solution was obtained. In order to measure the solubility of zeaxanthin in different solvents (shown in Table 7 below), a 5.0 ml portion of the saturated supernatant was filtered, desolventized, and the residues weighed. The values were compared with published values for lutein in the table below.

TABLE 7

Solubility of Zeaxanthin in Solvents.

| solvent | Zeaxanthin solubility (mg/L) | Lutein solubility (mg/L; Craft, 1992) |
|---|---|---|
| THF | >20,355 | 8000 |
| DCM | 2956 | 800 |
| Acetone | 1631 | 800 |
| EtOAc | 1069 | 800 |
| MtBE | 726 | 2000 |
| Methanol | 82 | 200 |
| IPA | 81 | 400 |
| Hexane | 68 | 20 |
| EtOH | 40 | 300 |

Abbreviations used in Table 7 are THF = tetrahydrofuran, DCM = dichloromethane, EtOAc = ethyl acetate, MtBE = methyl tert-butyl ether, IPA = isopropyl alcohol or 2-propanol, EtOH = ethanol.

Example 12

Demonstrating a solvent swap with heptane.

In a procedure identical to that described in Example 6, after distilling then refluxing for five hours, rather than decanting away the supernatant (which contains in solution 10-20% of zeaxanthin input as a mixture of cis and trans), the mixture was continuously distilled while heptane was added ("solvent swap"). Once the temperature of the distillate reached 75° C. the mixture was allowed to cool and a quantitative yield of zeaxanthin was present in a low-purity precipitate. One skilled in the art could further purify the precipitate by washing with solvents (such as alcohols) and/or water.

Example 13

Demonstrating the effect of number of water washes, number of methanol washes, and size of the methanol washes on the yield and purity of the isolated precipitate.

A set of experiments were carried out on a process identical to that described in Example 6. The results are presented in the table below. There appears to be an increase in both purity and yield when two water washes are carried out compared with only one water wash. It should be noted that attempts to carry out a third water wash resulted in a persistent emulsion that did not settle even after several days. The relatively low yields obtained after one water wash are to some degree reflective of the poor solids compaction obtained after only one water wash.

TABLE 8

Effect of one vs. two water washes and number and size of methanol washes on zeaxanthin purity and yield in isolated precipitate.

| #H2O washes | #MeOH Washes | MeOH wash volume | purity (wt % ZX) | yield |
|---|---|---|---|---|
| 1 | 1 | 3X | 14.3% | 28% |
| 1 | 1 | 9X | 14.3% | 27% |
| 1 | 3 | 3X | 54.5% | 24% |
| 1 | 3 | 9X | 67.1% | 18% |
| 2 | 1 | 3X | 17.3% | 51% |
| 2 | 1 | 9X | 20.5% | 49% |
| 2 | 3 | 3X | 66.1% | 48% |
| 2 | 3 | 9X | 70.3% | 39% |

Example 14

In a procedure similar to that described in Example 7, a solvent other than methanol is added during and/or prior to the distillation. The solvent (heptane, ethanol, isopropyl alcohol, n-propanol, butanol, etc.) is continuously added and the water content and precipitate settling time are monitored until a minimal settling time is achieved. One skilled in the art can maximize the compaction and yield for each solvent combination.

Example 15

In a procedure similar to that described in Example 9, acids other than $H_2SO_4$ are used, and the solid/liquid separation is carried out at various pH values. Acids include phosphoric, acetic, hydrochloric, formic, hydrobromic, trifluoroacetic, toluenesulfonic and methanesulfonic and the like. The relative yield of zeaxanthin in the solution and in precipitated form are determined at several different pH values for each acid. One skilled in the art can maximize the compaction and yield for each acid used.

Example 16

Application of Ausich, et al. Conditions to Todd et al. *Capsicum*.

Ausich, et al., (U.S. Pat. No. 5,648,564) describe a saponification process for isolating free-form zeaxanthin from Chinese wolfberries using propylene glycol. The Ausich, et al., process was conducted as described using the Todd et al. *Capsicum* plant material. Todd et al. *Capsicum* oleoresin (41 grams) was mixed with 41 grams of propylene glycol at 55° C. Then, 18 grams of 45% potassium hydroxide was added slowly over a 10 minute time frame, raising the temperature to 70° C., and maintaining that temperature for about 18 hours. The reaction was checked for completion via HPLC and was found to be 98.9% complete. The reaction mixture was then diluted to 10% of its' original concentration with water, and mixed at a steady 70° C. The mixture was then vacuum filtered at 70° C. to recover precipitate. A total of 1.9105 g of precipitate was collected, corresponding to a yield of 54.6% and having a purity of 31.6%. The resulting xanthophyll composition does not meet the finished product needs for purity, yield, ease of use, industrial compatibility and cost that are required to make product suitable for the nutritional supplement, food and beverage industries.

Example 17

Chinese wolfberry oleoresin is subjected to a similar procedure as that presented in Example 2, and one skilled in the art can modify the conditions to optimize the yield and purity of free-form zeaxanthin.

Example 18

Hauptmann, et al., (U.S. Pat. No. 6,784,351) disclose a mutant marigold which expresses zeaxanthin at high levels, where zeaxanthin is the dominant carotenoid pigment. Oleoresin made from such marigold is subjected to a similar procedure as that presented in Example 2, and one skilled in the art can modify the conditions to optimize the yield and purity of free-form zeaxanthin.

Example 19

The total carotenoids present in various samples and fractions were estimated spectrophotometrically by assuming the accepted extinction coefficient for zeaxanthin (2350). For example, the % total carotenoids in the solid paste obtained from the hexane layer in Example 6 were measured by taking a small amount of material and diluting in 20,000 parts solvent (hexane/THF). The procedure was carried out in duplicate and an average of the two values was taken.

TABLE 9

Duplicate calculation of % carotenoids for desolventized hexane layer from Example 6.

| Run | mass | dilution | ABS @ 450 nm | % carotenoids | |
|---|---|---|---|---|---|
| 1 | 0.2200 | 20000 | 0.4202 | 16.26% | |
| 2 | 0.3096 | 20000 | 0.6228 | 17.12% | |
| | | | | 16.69% | <-- Average |

The calculation is based on Beer's law (A=ebc), which allows the concentration of a given substance to be calculated from its absorbance.

Example 20

In order to determine free-form zeaxanthin content in various samples derived from *Capsicum*, the following procedure was carried out:

Calibration Curve:

An authentic standard of free-form trans-zeaxanthin was purchased from Indofine Chemical (part #020307S) and used to prepare the calibration curve. This method was standardized by absorbance using an E1% of 2350 in hexanes to calculate concentration of standards. Relative response factors for cis-isomers were taken to be 1.0, and total content of cis-zeaxanthin was determined by summing the values determined for di-cis-zeaxanthin, 9-cis-zeaxanthin, 13-cis-zeaxanthin, and 15-cis-zeaxanthin. The calibration curve was forced through zero.

Sample Preparation for Determination of Zeaxanthin Content in *Capsicum* Oleoresin:

1) About 400 mg of oleoresin was accurately weighed into a 50 mL volumetric flask and filled to mark with tetrahydrofuran.
2) To a culture tube were added: 600 µL of ethanol, 100 µL of 10% pyrogallol reagent, 250 µL of 40% methanolic potassium hydroxide.

3) A stream of nitrogen was applied to the tube for 15 seconds and then 100 μL of sample solution prepared in step 1 were added.
4) The tube was blanketed with nitrogen, capped tightly, and vortexed for 15 seconds, then refrigerated for 18 hours.
5) After 18 hours in the refrigerator, the sample was allowed to come to room temperature for 30 minutes.
6) 2.0 mL of 35% saturated sodium chloride solution was added to the culture tube.
7) 4.5 mL of tetrahydrofuran/hexane (1:4 v/v) were added and sample was vortexed for 30 seconds.
8) After sitting for 3-5 minutes, two distinct immiscible layers appeared.
9) The supernatant was decanted from culture tube with transfer pipette into a 10.0 mL volumetric flask.
10) 4.5 mL of tetrahydrofuran/hexane (1:4 v/v) were added and sample was vortexed for 30 seconds.
11) Steps 8-9 were repeated until the supernatant was colorless.
12) The 10.0 mL volumetric flask containing supernatant from the liquid-liquid extractions was filled to the mark with hexane.
13) The solution from step 12 was assayed directly by HPLC.

Figure 1:
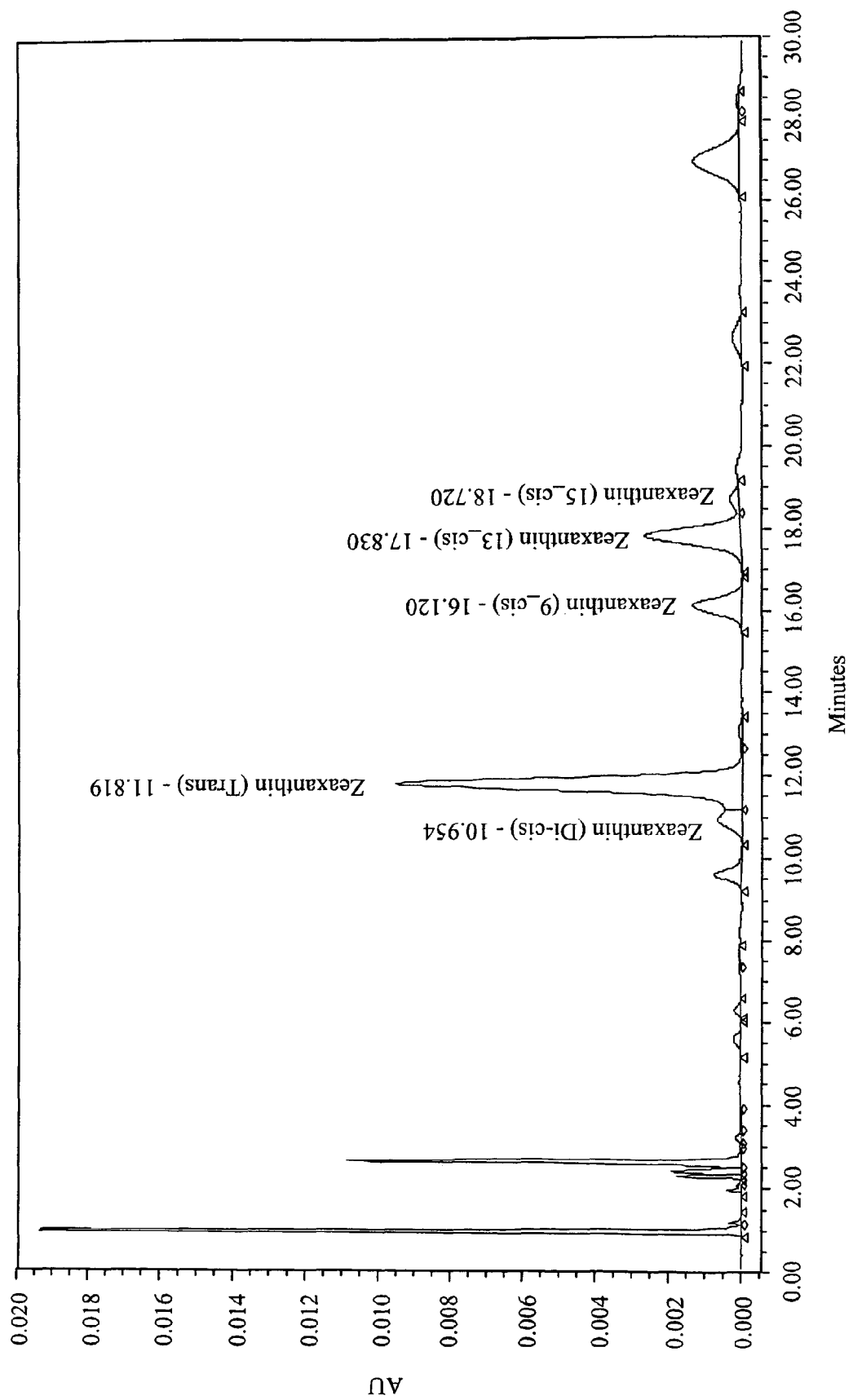
FIG. 1. Determination of zeaxanthin content in *Capsicum* oleoresin by HPLC.

Determination of zeaxanthin content in *Capsicum* oleoresin by HPLC: After employing the sample preparation procedure outlined above to the starting oleoresin for the experimental examples presented herein, and the HPLC conditions detailed below, a chromatogram similar to that presented in FIG. 1 was generated.

Sample preparation for determination of zeaxanthin content in experimental saponification products:
1) A small amount of sample was accurately weighed into a borosilicate glass vial.
2) The sample was dissolved in tetrahydrofuran containing 2% acetic acid.
3) A small portion of the solution from step 2 was transferred to another vial, then diluted further with a mixture of hexane:tetrahydrofuran (4:1 v/v) such that the absorbance at 450 nm is about 1.0, as measured on a Beckman-Coulter DU800 spectrophotometer.
4) The diluted solution produced in step 3 was assayed directly by HPLC.

Determination of zeaxanthin content in experimental saponification products by HPLC:
After diluting the material as described above, the sample is analyzed by HPLC following the parameters detailed below. Typical chromatograms for both isolated precipitates and for supernatants are presented in FIG. 2.

The chromatograms shown are for the corresponding outputs of reaction #17 in Table 3 of Example 1. The large peak eluting around 12 minutes corresponds to all-trans-zeaxanthin. This procedure was used for quantitative determination of zeaxanthin in outputs (solids, supernatants, wash solutions) as well as for determining total reaction yield (HPLC yield).

Stability of cis and trans isomers of zeaxanthin to the sample preparation conditions:
Using the sample preparation conditions above, duplicate samples were prepared from the same oleoresin and each were split into seven separate vials and then stored in the refrigerator. A vial from each of the duplicate samples was removed at various times and analyzed by HPLC. The purpose was to ensure that the cis and trans isomer concentrations were stable and not changing as a function of time under the analytical saponification conditions and subsequent HPLC analyses. The data in Table 10 show that the amounts of cis and trans isomers do not change under the sample preparation conditions. Note that the typical saponification time is about 18 hours and that no change was observed between 2 and 119 hours under these conditions. We therefore conclude that our sample preparation and analysis conditions are not changing the amounts of the two isomers and that the amounts measured are the amounts in the samples prior to sample preparation and analysis.

TABLE 10

Amounts of cis and trans Isomers of Zeaxanthin.

| Time Saponifying in Refrigerator (hours) | % Cis zea | % Trans Zea | % Total Zea |
|---|---|---|---|
| 2 | 0.034 | 0.412 | 0.446 |
| 2 | 0.033 | 0.417 | 0.450 |
| 4 | 0.033 | 0.413 | 0.446 |
| 4 | 0.035 | 0.420 | 0.455 |
| 7 | 0.034 | 0.413 | 0.447 |
| 7 | 0.033 | 0.415 | 0.448 |
| 23 | 0.033 | 0.411 | 0.444 |
| 23 | 0.033 | 0.416 | 0.449 |
| 30 | 0.033 | 0.412 | 0.445 |
| 30 | 0.033 | 0.417 | 0.450 |
| 54 | 0.033 | 0.413 | 0.446 |
| 54 | 0.034 | 0.410 | 0.444 |
| 119 | 0.036 | 0.415 | 0.451 |
| 119 | 0.035 | 0.414 | 0.449 |

Other parameters are as follows:
HPLC: Waters 2695 Separations System
Database: Empower (Build 1154) Software
Detector: Waters 2487 Dual-wavelength Detector—Single Wavelength at 450 nm./Sampling Rate=5/Filter=Hamming/AUFS=2.0/Time Const=1.0
HPLC Column: ES Industries Chromegabond Diol 3 um 60 A–15 cm×4.0 mm (Cat#:134111D) with a Phenomenex security guard column holder (Cat#:KJO-4282) containing a NH2 filter (Cat#:AJO-4301). PSI @ initial conditions=1500 Δ6
Pump: Isocratic Method at 1.5 mL/min
Mobile Phase Hexane with 4% Isopropyl alcohol
Run Time: 30.0 min
Injection Volume: 20 μL Example 21

In an experiment identical to the procedure described in Example 6, the zeaxanthin/methanol slurry was desolventized using a spray dryer. No degradation of zeaxanthin was observed at any dryer settings tested. Inlet temperatures ranged from 120° C. to 160° C., outlet temp was 60.5° C. to 87.2° C., and rotary atomizer was set at 5.5 bar. Nitrogen was used as the drying gas.

Example 22

A portion of the methanol/zeaxanthin slurry, which in Example 6 was dried down as the final step in the process, was centrifuged and decanted and the solid cake thereby obtained was diluted with 99 parts water. This aqueous slurry containing approximately 1% solids was spray-dried to afford a powder with similar purity as for the original material. In a similar vein, one skilled in the art distills away methanol and replaces the methanol with water, and such a water/zeaxanthin slurry, amenable to a non-explosion-proof spray dryer, is spray-dried with similar results.

Example 23

To 20 grams of Todd et al. *Capsicum* oleoresin were added 40 ml of heptane, 40 ml isopropyl alcohol, and 20 ml of KOH (45% aq.). The reaction mixture was stirred overnight at which time it was transferred to a separating funnel along with 10 ml heptane, 10 ml isopropyl alcohol, and 20 ml water. The low-color lower phase was removed and the remaining mixture was centrifuged to afford a supernatant and an isolated precipitate. After desolventizing, the precipitate weighed 10.108 grams. With no further processing other than desolventization, the isolated precipitate had a purity of 2.9% corresponding to a yield of 48%.

Example 24

In a procedure similar to that presented in Example 2, paprika oleoresin (20.01 g) containing 4.95% total zeaxanthin which was 0.86% cis-zeaxanthin (mixture of isomers) was subjected to the same reagents, proportions, and reaction conditions given in Example 2, including 24 hour reflux, removal of hexane/carotene layer, water washes, addition of methanol and removal by distillation of hexanes. The mixture was centrifuged to separate the crude precipitate from the liquid supernatant. The crude precipitate was washed once by homogenizing with methanol (57 ml) followed by centrifugation to afford a refined precipitate and a wash solution. After desolventization of the refined precipitate, 1.2836 g of a fine red-orange powder containing 57.7% by weight all-trans-zeaxanthin was obtained, corresponding to a 75% isolated yield. Thus a 5% zeaxanthin oleoresin provides similar purity and yields to 2.7% zeaxanthin oleoresin.

Example 25

In a procedure similar to that presented in Example 2, paprika oleoresin containing at least about 5% total zeaxanthin which is ≧70% trans-zeaxanthin (mixture of isomers) is subjected to the same reagents, proportions, and reaction conditions given in Example 2, including 24 hour reflux, removal of hexane/carotene layer, water washes, addition of methanol and removal by distillation of hexanes. The mixture is centrifuged to separate the crude precipitate from the liquid supernatant. The crude precipitate is washed once by homogenizing with methanol followed by centrifugation to afford a refined precipitate and a wash solution. After desolventization of the refined precipitate, a fine red-orange powder containing >40% by weight all-trans-zeaxanthin is obtained, corresponding to a >60% high-purity, isolated yield.

Example 26

Effect of various additives on isolated product.
Referring to Example 6, a portion of the material remaining after decanting away the hexane/carotene layer was subjected to various washing procedures. Initially, for qualitative evaluation, a small amount of sample (ca. 10 ml) was added to each of four vials and individually mixed with the following additives: 3 ml calcium acetate (10% aq.), 3 ml ethylenediamine tetraacetic acid (10% aq.), 3 ml phytic acid (10% aq.), and 3 ml pure water (control). The vials were capped, gently inverted a few times and allowed to settle. Except for the calcium acetate vial, all of them formed a distinct lower aqueous phase ('wash phase') within a few hours. With calcium acetate, however, the sample formed a persistent emulsion, therefore washing the sample with calcium acetate was not investigated quantitatively. The other additives were investigated quantitatively by using the aqueous solution of the given additive rather than pure water in the water-washing steps described in Example 6. The results are presented in Table 11 below:

| Additive | purity total zeaxanthin | yield % zeaxanthin isolated as powder |
|---|---|---|
| EDTA (10% aq.) | 51.8% | 78% |
| phytic acid (10% aq.) | 7.8% | 48% |
| water (control) | 53.7% | 83% |

As shown in the Table 11, none of the additives provided any noticeable improvement over pure water, in terms of purity or yield of isolated zeaxanthin.

The present invention is not to be limited in scope by the specific embodiments described herein. Indeed, various modifications of the invention in addition to those described herein will become apparent to those skilled in the art from the foregoing description.

All patents, applications, publications, test methods, literature, and other materials cited herein are hereby incorporated by reference.

REFERENCES

S. M. Moeller, P. F. Jacques, J. B. Blumberg, *Journal of the American College of Nutrition* (2000) 19, 522S-527S.

Seddon, *J. Amer. Med. Assoc.* (1994) 272 (18), 1413-1420.

M. Chopra, D. I. Thurnham, *Proceedings of the nutrition Society* (1994) 53, 1993 #18A.

A. N. Howard, N. R. Williams, C. R. Palmer, J. P. Cambou, A. E. Evans, J. W. Foote, *International Journal of Vitamin and Nutrition Research* (1996) 66, 113-118.

Morris, *J. Amer. Med. Assoc.* (1994) 272 (18), 1439-1441.

B. P. Chew, M. W. Wong, T. S. Wong *Anticancer Research* (1996) 16, 3689-3694.

T. Wingerath, W. Stahl, and H. Sies, *Archives of Biochemistry and Biophysics*, Volume 324, Number 2, December 1995, pp. 385-390(6)

Andreas Schieber, Reinhold Carle, *Trends in Food Science and Technology* (2005) 16, 416-422.

Milind Kesharlal Biyani, Jhawar Ramesh Chandra, World Pat. Appl. Pub. No. 00/16792, Published Mar. 30, 2000.

Morris Zelkha and Tanya Sedlov, U.S. Pat. No. 6,797,303, Issued Sep. 28, 2004.

Rodney L. Ausich and David J. Sanders, U.S. Pat. No. 5,648,564, Issued Jul. 15, 1997.

Benedikt J. Sas and Clifford Adams, U.S. Pat. No. 5,876,782, Issued Mar. 2, 1999.

Peter M. Grant, U.S. Pat. No. 3,523,138, Issued Aug. 4, 1970.

Frederick Khachik U.S. Pat. No. 5,382,714, Issued Jan. 17, 1995.

Frederick Khachik, U.S. Pat. No. 6,262,284, Issued Jul. 17, 2001.

Mieko Kimura, Delia B. Rodriguez-Amaya, Helen T. Godoy, *Food Chemistry*, (1990) 35, 187-195.

F. Granado, B. Olmeidlla, E. Gil-Martinez, I. Blanco, *Journal of Food Composition and Analysis* (2001) 14, 479-489.

Ricardo Montoya-Olvera, Juan-Roberto Elizondo-Mireles, Carlos-Javier Torres-Gomez, Jose-Odon Torres-Quiroga, U.S. Pat. No. 6,504,067 B1, Issued Jan. 7, 2003.

Sunil Bhaskaran, Vishwaraman Mohan, U.S. Pat. No. 7,179,930 B2, Issued Feb. 20, 2007.

Doddabele L. Madhavi, Daniel I. Kagan, U.S. Pat. No. 6,380,442 B1, Issued Apr. 30, 2002.
Sunil Kumar T. K., Sherena P. Abdnlkandir, Sajoy Sebastian, U.S. Pat. No. 6,743,953 B2, Issued Jun. 1, 2004.
Juliusz K. Tyczkowski, Pat B. Hamilton, *Poultry Science* (1991) 70, 651-654.
Benedikt Sas, Clifford Adams, U.S. Pat. No. 6,221,417 B1, Issued Apr. 24, 2001.
Ana Rodriquez-Bernaldo de Quiros and Helena S. Costa, *Journal of Food Composition and Analysis* (2006) 19, 97-111.
F. Khachik, G. R. Beecher, N. F. Whittaker, *J. Agric. Food Chem.* (1986) 34, 603-616.
F. Granado, B. Olmedilla, I. Blanco, E. Rojas-Hidalgo, *J. Agric. Food Chem.* (1992) 40, 2135-2140.
K. J. Scott, *Food Chemistry* (1993) 45, 357-364.
D. J. Hart and K. J. Scott, *Food Chemistry* (1995) 54, 101-111.
Erik Larsen and Lars P. Christensen, *J. Agric. Food Chem.* (2005) 53, 6598-6602.
Muhammed Majeed, Robert B. Murray, World Pat. Pub. No. WO 02/060865 A1, Published Aug. 8, 2002.
Gustavo Rodriguez Pena, U.S. Pat. Appl. Pub. No. US 2007/0161826 A1, Published Jul. 12, 2007.
Xinde Xu, Bin Shao, Di Zhou, Shuangming Xe, Yanfeng Wang, Boqui Chen, U.S. Pat. Appl. Pub. No. US 2007/0032683 A1, Published Feb. 8, 2007.
Sethuraman Swaminathan, Kunhiraman Priya Madavalappil, WO Pat Appl. Pub. No. 2006/114794 A1. Published Nov. 2, 2006.
Jose Antonio Socla Rosales, M. C. Mario D. Torres Cardona, U.S. Pat. No. 7,150,890 B2, Issued December 19, 2006.
Mark Hoffman, David Baugh, Michael Ahern, David Walsh, U.S. Pat. No. 7,109,361 B2, Issued Sep. 19, 2006.
Harapanahalli S. Muralidhara, U.S. Pat. No. 5,602,286, Issued Feb. 11, 1997.
Gustavo Rodriguez, U.S. Pat. No. 5,973,211, Issued Oct. 26, 1999.
Nuria Sanroma Virgili, Joan Charles Ferater Martorell, Mildred De Bloos De Clercq, Juan A. Fernandez Martin, U.S. Pat. No. 5,998,678, Issued Dec. 7, 1999.
Mario-David Torres-Cardona, Jose Torres-Quiroga, U.S. Pat. No. 5,523,494, Issued Jun. 4, 1996.
Kurt Bernhard, Stephan Jaggli, Paul Kreienbuhl, Ulrich Schwieter, U.S. Pat. No. 4,883,887, Issued Nov. 28, 1989.
Frederick Khachik, U.S. Pat. No. 7,173,145, Issued Feb. 6, 2007.
M. Isabel Minguez-Mosquera, Damasco Hornero-Mendez, *J. Agric. Food Chem.* (1993) 41, 1616-1620.
Inami Osamu, Tamura Itaru, Yajima Izumi, Jap. Pat. Appl. No. 57-133160, Published Aug. 17, 1982.
Yoshikura Masahiro, Washino Ken, Jap. Pat. Appl. No. 58-173164, Published Oct. 12, 1983.
Inami Osamu, Tamura Itaru, Yajima Izumi, Jap. Pat. Appl. No. 57-180663, Published Nov. 6, 1982.
A. Lawrence Curl *Agricultural and Food Chemistr*, Vol 10, No. 6, November-December 1962.
A. Lawrence Curl *Agricultural and Food Chemistr*, Vol 12, No. 6, November-December 1964.
A. Lawrence Curl *Agricultural and Food Chemistr*, Vol 1, No. 6, Jun. 10, 1953.
Gustavo Rodriguez, Mario-David Torres-Cardona, Alejandro Diaz, U.S. Pat. No. 6,329,557, Issued Dec. 11, 2001.
Paul H., Todd, Carrie K. Young, Carol L. Locey, James P. Barren, Anthony P. Vandenhombergh, Donald R. Berdahl, Jeffrey S. Kanel, U.S. Pat Appl. Pub. No. US 2006/0185034 A1, Published Aug. 17, 2006.
N. R. Farnsworth, Ed. NAPRALERT: A database of world literature of natural products, Program for Collaborative Research in the Pharmaceutical Sciences, College of Pharmacy, University of Illinois at Chicago. Accessible online; Searches performed through Sep. 13, 2007.
G. Englert, K. Noack, E. A. Broger, E. Glinz, M. Vecchi, *Helvetica Chimica Acta* (1991) 74, 969-982.
O. Isler, H. Lindlar, M. Montaven, R. Ruegg, P. Zeller, *Helvetica Chimica Acta* (1956), 27, 249-259.
Karrer, P. and Jucker, E., 1950, Carotenoids, Elsevier Publ. Co., Znc., Amsterdam, pp. 38-42, 180 ff.
O. Isler, H. Lindlar, M. Montavon, R. Ruegg, P. Zeller, U.S. Pat. No. 2,849,507, Issued Aug. 26, 1958.
J. D. Surmatis, U.S. Pat. No. 3,441,623, Issued Apr. 29, 1969.
Zechmeister, L., 1962, Cis-Trans Isomeric Carotenoids Vitamins A and Arylpolyenes, Academic Press, pp. 46-57.
Joseph Donald Surmatis, U.S. Pat. No. 3,989,757, Issued Nov. 2, 1976.
Antony et al., 2001, U.S. Pat. No. 6,784,351
Hauptmann, et al., U.S. Pat. No. 6,784,351.

The invention claimed is:

1. A method for converting esterified xanthophylls from *Capsicum* into their non-esterified form comprising the steps of:
   a) contacting xanthophyll esters in an oleoresin with a hydrocarbon, with an oleoresin to hydrocarbon ratio of 1:0.5 to 1:10 (weight/weight), wherein the hydrocarbon is hexane or a mixture of low boiling hydrocarbons;
   b) adding an alcohol at an oleoresin:alcohol ratio of 1:1 to 1:10 (weight/weight);
   c) adding a base at an oleoresin:base ratio of 10:1 to 1:1 (weight/weight);
   d) applying a blanket of an inert gas, selected from, but not limited to nitrogen and argon;
   e) applying heat, if necessary, to at least 20° C. up to reflux temperature;
   f) allowing the mixture to stir and/or reflux under the inert atmosphere for 0.25 to 120 hrs;
   g) reducing the temperature of the reaction mixture to 0° to 50° C.;
   h) allowing the mixture to settle for 0.1 to 1000 hours;
   i) removing the upper hydrocarbon phase rich in carotenes, including alpha-carotene, beta-carotene, lycopene, and the xanthophyll, beta-cryptoxanthin;
   j) optionally adding more hydrocarbon to the remaining reaction mixture with stirring and repeating steps h) and i);
   k) desolventizing the upper hydrocarbon phase(s) to obtain a carotene concentrate;
   l) adding water, optionally mixed with an alcohol and/or complexing or chelating agent, to the lower phase remaining after hydrocarbon removal, with an oleoresin:water ratio of 1:0.1 to 1:5 (weight/weight), then thoroughly mixing;
   m) allowing the system to settle undisturbed for 0.5 to 1000 hours;
   n) draining the lower aqueous phase (first water wash) rich in soaps and other polar soluble materials;
   o) optionally repeating steps l) through n), one or more times;
   p) adding an alcohol to the mixture, optionally adjusting the water content of the mixture to 1-15%, by alcohol addition and/or concurrent or subsequent distillation;
   q) optionally removing the remaining hydrocarbon via distillation;

r) separating the solid precipitated xanthophylls from the liquid supernatant by decanting, centrifugation, or filtration;
s) adding to the solid xanthophylls, a wash solvent and mixing to form a slurry;
t) separating the solid xanthophylls from the wash solvent, by decanting or centrifuging;
u) optionally repeating steps s) and t) until the required purity is achieved;
v) removing the solvent(s) and drying;
w) packaging the dried xanthophylls obtained in the preceding step in an inert environment, selected from vacuum packaging or packaging inerted with nitrogen or argon;
x) optionally, precipitating more solid xanthophylls from the liquid supernatant generated in steps r) and t) by addition of water and/or allowing the supernatant to stand for one or more days, and isolating the precipitate thereby formed by filtration, centrifugation, and/or decantation;
y) optionally repeating step x) until no more precipitate is formed; and
z) optionally desolventizing at step x) to recover the xanthophylls;
aa) optionally adding an antioxidant to the mixture prior to desolventizing at steps v), and/or x) and/or z);
ab) optionally extracting the xanthophylls from the precipitate at steps v), and/or x), and/or z) with a suitable solvent such as methylene chloride prior to desolventization; and
ac) optionally adding water to the precipitate in step ab) prior to extracting;
ad) optionally raising the temperature of the mixture to 40° to 60° after draining the water in step n) and isolating the zeaxanthin rich precipitate layer which forms at the bottom of the vessel;
ae) optionally repeating steps z), aa), ab) and/or ac) with the precipitate layer formed in step ad).

2. The method of claim 1, wherein the ratio of oleoresin to hydrocarbon is 1:1.5 (weight/weight) in step a).

3. The method of claim 1, wherein the ratio of oleoresin to alcohol is 1:3 (weight/weight) in step b).

4. The method of claim 1, wherein the alcohol is methanol in step b).

5. The method of claim 1, wherein the ratio of oleoresin to base is a 1:1.2 ratio (weight/weight) of oleoresin:potassium hydroxide, with potassium hydroxide added as a 45% aqueous solution in step c).

6. The method of claim 1, wherein the temperature in step e) is 50°-80° C.

7. The method of claim 1, wherein the number of hours in step f) is 24 hrs.

8. The method of claim 1, wherein the reduced temperature in step g) is 20°-25° C.

9. The method of claim 1, wherein the number of hours allowed to settle in step h) is 0.5 hours.

10. The method of claim 1, wherein the ratio of oleoresin to water in step l), is 1:1.5 (weight/weight).

11. The method of claim 1, wherein the number of hours in step m) is 4 hours.

12. The method of claim 1, wherein the water content of the mixture in step p) is 2.8%.

13. The method of claim 1, rein the solvent in step v) or step z) is removed by spray drying, 14. The method of claim 1, wherein the solvent in step v) is removed by dilution with water and optionally removing the solvent via distillation, decantation, or centrifugation, prior to drying.

15. The method of claim 1, wherein the wash solvent in step s) and/or u) is methanol.

16. The method of claim 1, wherein the wash solvent in step s) and/or u is ethanol.

17. The method of claim 1, wherein the wash solvent in step s) and/or u) is an alcohol having 1 to 4 carbons.

18. The method of claim 1, wherein the wash solvent is a hydrocarbon.

19. The method of claim 1, wherein the xanthophyll is zeaxanthin,

20. The method of claim 1, wherein the purified carotenoids so obtained are formulated and stabilized in bulk, in the form of powder, beadlets, granules, oil dispersions and/or water dispersions.

21. The method of claim 1, wherein a co-product comprises beta-carotene, alpha-carotene, beta-cryptoxanthin or a mixture thereof in step k).

22. The method of claim 1, wherein the base is sodium hydroxide.

23. The method of claim 1, wherein the base is a hydroxide with an alkaline earth metal counterion.

24. The method of claim 1, wherein the base is a carbonate with an alkali or alkaline earth metal counterion.

25. The method of claim 1, wherein the base is an alkoxide with an alkali or alkaline earth metal counterion.

* * * * *

UNITED STATES PATENT AND TRADEMARK OFFICE
CERTIFICATE OF CORRECTION

| | |
|---|---|
| PATENT NO. | : 8,247,615 B2 |
| APPLICATION NO. | : 12/800416 |
| DATED | : August 21, 2012 |
| INVENTOR(S) | : Mark Reilly et al. |

It is certified that error appears in the above-identified patent and that said Letters Patent is hereby corrected as shown below:

| | |
|---|---|
| Title Page, item (56); References Cited, KLAUI: | "3,206,316" should be --3,206,315--. |
| References Cited, SAS: | "5,876,782" should be --5,876,792--. |
| Other Publications, ENGLERT: | "74:959-982" should be --74:569-982--. |
| Column 52, Line 15, Claim 13: | "rein" should be --wherein--. |

Signed and Sealed this
Twenty-seventh Day of November, 2012

David J. Kappos
*Director of the United States Patent and Trademark Office*